United States Patent
Cheng et al.

(10) Patent No.: US 10,214,780 B2
(45) Date of Patent: Feb. 26, 2019

(54) METHOD AND MEANS FOR IDENTIFICATION OF ANIMAL SPECIES

(71) Applicant: CITY UNIVERSITY OF HONG KONG, Hong Kong (CN)

(72) Inventors: Shuk Han Cheng, Hong Kong (CN); Chun Chi Lin, Hong Kong (CN)

(73) Assignee: CITY UNIVERSITY OF HONG KONG, Kowloon Tong (HK)

(*) Notice: Subject to any disclaimer, the term of this patent is extended or adjusted under 35 U.S.C. 154(b) by 94 days.

(21) Appl. No.: 15/347,888

(22) Filed: Nov. 10, 2016

(65) Prior Publication Data
US 2017/0088903 A1    Mar. 30, 2017

Related U.S. Application Data

(63) Continuation-in-part of application No. 13/777,308, filed on Feb. 26, 2013, now abandoned.

(60) Provisional application No. 61/608,824, filed on Mar. 9, 2012.

(51) Int. Cl.
*C12Q 1/68*     (2018.01)
*C12Q 1/6888*   (2018.01)

(52) U.S. Cl.
CPC .................... *C12Q 1/6888* (2013.01)

(58) Field of Classification Search
None
See application file for complete search history.

(56) References Cited

U.S. PATENT DOCUMENTS

| | | | |
|---|---|---|---|
| 6,858,387 B1 | 2/2005 | Smith | |
| 2006/0019295 A1 | 1/2006 | Presting | |

FOREIGN PATENT DOCUMENTS

| | | | | |
|---|---|---|---|---|
| JP | 2009195226 | A1 | 3/2009 | |
| JP | 2009195226 | * | 9/2009 | ............... C12Q 1/68 |
| WO | 2003/048723 | A2 | 6/2003 | |
| WO | 2008/056325 | A2 | 5/2008 | |

OTHER PUBLICATIONS

Chou CC, Chen CH, Lee TT, Peck K. Optimization of probe length and the number of probes per gene for optimal microarray analysis of gene expression. Nucleic Acids Res. Jul. 8, 2004; 32(12):e99 pp. 1-8. (Year: 2004).*
Chung IH, Yoo HS, Eah JY, Yoon HK, Jung JW, Hwang SY, Kim CB. A DNA microarray for identification of selected Korean birds based on mitochondrial cytochrome c oxidase I gene sequences. Mol Cells. Oct. 2010; 30(4):295-301. Epub Sep. 2, 2010. (Year: 2010).*
English Translation of JP2009-195226 by Kusama Toyoko (Year: 2009).*
Hajibabaei M, Singer GA, Clare EL, Hebert PD. Design and applicability of DNA arrays and DNA barcodes in biodiversity monitoring. BMC Biol. Jun. 13, 2007; 5:24.pp. 1-7. (Year: 2007).*
Gill, Peter, Alec J. Jeffreys and David J. Werrett. "Forensic application of DNA 'fingerprints'." Nature, vol. 318, Dec. 12, 1985. pp. 577-579.
Lockley, A.K., and R.G. Bardsley. "DNA-based methods for food authentication." Trends in Food Science and Technology, vol. 11, 2000. pp. 67-77.
Handy, Sara M. et al. "A Single-Laboratory Validated Method for the Generation of DNA Barcodes for the Identification of Fish for Regulatory Compliance." Journal of AOAC International, vol. 94, No. 1, 2011. pp. 201-210.
Meusnier, Isabelle et al. "A universal DNA mini-barcode for biodiversity analysis." BMC Genomics, 9:214, 2008.
Shokralla, Shadi et al. "Pyrosequencing for Mini-Barcoding of Fresh and Old Museum Specimens." PLoS One 6(7): e21252. doi:10.1371/journal.pone.0021252 (Jul. 2011).
Cheng-Chung Chou et al. "Optimization of probe length and the number of probes per gene for optimal microarray analysis of gene expression." Nucleic Acids Research, 2004, vol. 32, No. 12.
Walker et al. "Molecular Biomethods Handbook, $2^{nd}$ Edition, 2008, p. 41-53, Chapter: Probe Design, Production, and Applications."
Chung, IH, Yoo HS, Eah JY, Yoon HK, Jung JW, Hwang SY, Kim CB, A DNA microarray for identification of selected Korean birds based on mitochondrial cytochrome c oxidase I gene sequences. Mol Cells. Oct. 2010; 30(4):295-301. Epub Sep. 2, 2010.
Dawnay N, Ogden R, McEwing R, Carvalho GR, Thorpe RS, Validation of the barcoding gene COI for use in forensic genetic species identification, Forensic Sci Int Nov. 15, 2007; 173(1):1-6, Epub Feb. 14, 2007.
Hajibabaei M, Singer GA, Clare EL, Hebert PD. Design and applicability of DNA arrays and DNA barcodes in biodiversity monitoring. BMC Biol. Jun. 13, 2007; 5:24, pp. 1-7.
Hebert, PD, Cywinska A, Ball SL, deWaard JR, Biological Identifications through DNA barcodes, Proc Biol Sci. Feb. 7, 2003; 270 (1512):313-21.
Pfrender et al Assessing Macroinvertebrate Biodiversity in Freshwater Ecosystems: Advances and Challenges in DNA-based Approaches. The Quarterly Review of Biology, vol. 85, No. 3 (Sep. 2010), pp. 319-340.
Pozhitkov AE, Tautz D. An algorithm and program for finding sequence specific oligonucleotide probes for species identification. BMC Bioinformatics. 2002; 3:9. Epub Mar. 6, 2002: pp. 1-7.
Rychlik W, Rhoads RE. A computer program for choosing optimal oligonucleotides for filter hybridization, sequencing and in vitro amplification of DNA. Nucleic Acids Res. Nov. 11, 1989;17(21):8543-51.
Supplemental document 1 of Hajibabaei M, Singer GA, Clare EL, Hebert PD. Design and applicability of DNA arrays and DNA barcodes in biodiversity monitoring. BMC Biol. Jun. 13, 2007; 5:24, pp. 1-7.

(Continued)

*Primary Examiner* — Gary Benzion
*Assistant Examiner* — Olayinka A Oyeyemi
(74) *Attorney, Agent, or Firm* — Melvin Li; Heslin Rothenberg Farley & Mesiti PC

(57) ABSTRACT

The present invention is concerned with a method of rapid identification of a mammalian species origin or mammalian species origins of a sample.

5 Claims, 8 Drawing Sheets

Specification includes a Sequence Listing.

(56) References Cited

OTHER PUBLICATIONS

Supplemental document 2 of Hajibabaei M, Singer GA, Clare EL, Hebert PD. Design and applicability of DNA arrays and DNA barcodes in biodiversity monitoring. BMC Biol. Jun. 13, 2007; 5:24, pp. 1-7.

* cited by examiner

Figure 2

| Pork | | | | | | |
|---|---|---|---|---|---|---|
| | Ss60 P6a | Ss60 P6b | Ss60 P6c | Ss60 P6d | Ss60 P6e | Ss60 P9a |
| | Ss60 P5a | Ss60 P5b | Ss60 P5c | Ss60 P5d | Ss60 P5e | Ss60 P9b |
| | Ss60 P7A | Ss60 P7b | Ss60 P7c | Ss60 P7d | Ss60 P7e | Ss60 P10a |
| | Ss60 P4a | Ss60 P4b | Ss60 P4c | Ss60 P4d | Ss60 P4e | Ss60 P10b |
| | | Ss70 P5 | Ss70 P5b | Ss70 P6 | Ss70 P6b | |

| Beef | | | | | | |
|---|---|---|---|---|---|---|
| | Bt60 P12 | Bt60 P2 | Bt60 P3 | Bt60 P6A | Bt60 P6B | Bt60 P6C |

| Lamb | | | | | | |
|---|---|---|---|---|---|---|
| | Oa60 P7A | OA60 P7B | Oa60 P7C | Oa60 P7D | Oa60 P5A | Oa60 P5B |
| | Oa60 P5C | Oa60 P5D | Oa60 P4A | Oa60 P4B | Oa60 P4C | Oa60 P4D |
| | Oa60 P6A | Oa60 P6B | Oa60 P6C | Oa60 P6D | Oa70 P2 | Oa70 P3 |

| Horse | | | | | | |
|---|---|---|---|---|---|---|
| | | Ec60 P1 | Ec60 P2 | Ec60 P3 | Ec60 P4 | Ec60 P5 |
| | Ec60 P6 | Ec60 P7 | Ec60 P13 | Ec60 P14 | Ec60 P15 | Ec60 P16 |
| | Ec60 P17 | Ec60 P18 | Ec60 P8A | Ec60 P8B | Ec60 P9A | Ec60 P9B |
| | Ec60 P10A | Ec60 P10B | Ec60 P11A | Ec60 P11B | Ec60 P12A | Ec60 P12B |
| | | Ec70 P6 | Ec70 P6B | Ec70 P7 | Ec70 P7B | |
| | | Ec70 P8 | Ec70 P8B | Ec70 P9 | Ec70 P9B | |
| | Ec70 P10 | Ec70 P10B | Ec70 P12 | Ec70 P13 | Ec70 P14 | Ec70 P15 |

| Dog | | | | | | |
|---|---|---|---|---|---|---|
| | | Cl60 P1A | Cl60 P1B | Cl60 P1C | Cl60 P2A | Cl60 P3A |
| | Cl70 P2 | Cl70 P2B | Cl70 P3 | Cl70 P3B | Cl70 P4 | Cl70 P4B |

| Cat | | | | | | |
|---|---|---|---|---|---|---|
| | Fc60 P2A | Fc60 P2B | Fc60 P2C | Fc60 P1A | Fc60 P3A | Fc60 P4A |
| | | Fc60 P6A | Fc70 P1 | Fc70 P2 | Fc70 P3 | |

| Mouse | | | | |
|---|---|---|---|---|
| | | Mm60 P1 | Mm60 P3A | Mm60 P4 | Mm60 P5 |
| | | Mm60 P6A | Mm60 P7 | Mm60 P8A | Mm60 P9A |
| | | Mm60 P10 | Mm60 P11 | Mm60 P12 | Mm60 P13 |
| | | Mm60 P14 | Mm60 P15 | Mm60 P16 | |
| | | Mm70 P1 | Mm70 P2 | Mm70 P3 | Mm70 P4 |

Figure 4

|  | Ss60 P9a | Ss60 P9b | Ss70 P6a | Ss70 P6b |  |
|---|---|---|---|---|---|
| Bt60 P12 | Bt60 P2 | Fc60 P1A | Fc60 P2A | Fc60 P2B | Fc60 P2C |
| Oa60 P6A | Oa60 P6B | Oa60 P6C | Oa60 P6D | Oa70 P2 | Oa70 P3 |
| Mm60 P3A | Mm60 P4 | Mm70 P1 | Mm70 P2 | Ec60 P1 | Ec60 P13 |
|  | Ec70 P12 | Ec70 P14 | Cl60 P1a | Cl60 P2a | Cl70 P2B |

METHOD AND MEANS FOR IDENTIFICATION OF ANIMAL SPECIES

CROSS REFERENCE TO RELATED APPLICATIONS

The present application is a continuation-in-part application of U.S. patent application Ser. No. 13/777,308 filed on Feb. 26, 2013 which claims priority from U.S. Patent Application Ser. No. 61/608,824 filed on Sep. 3, 2012, contents of which are incorporated herein in their entirety.

FIELD OF THE INVENTION

The present invention is concerned with a method of identification of species, and in particular a method of making relatively rapid identification of animal species including but not limited to *Bos Taurus* (cattle), *Sus scrofa* (pig), *Ovis aries* (sheep), *Equus caballus* (horse), *Canis lupus* (dog) and *Mus musculus* (mouse) and *Felis Catus* (cat). The present invention is also concerned with means for use in carrying out such method, and a method for engineering such means.

BACKGROUND OF THE PRESENT INVENTION

Due to a vast range of reasons, there has been a need of identifying animal species origin of a sample. For example, in the context of forensic investigation there is often the need of ascertaining the identity of an animal tissue sample in a crime scene. In the context of quality control of food manufacturing, there is a need to ascertain whether a food product claimed to contain certain type of animal meat is indeed what it is claimed to be. There are actually many other possible applications of using animal species origin or animal tissue identification methods, and one can also envisage that such applications can be very useful in medical science and pharmaceutical industry, and of course to address food safety issues as well.

There have been many methodologies seeking to address the needs of identification of animal species. While many of these methodologies have their unique characteristics, they often suffer from drawbacks, and tend to address some issues but not others. For example, some methodologies tend to be fairly accurate in their identification but at the expense of tremendous complexity in procedures. Some other methodologies are relatively simple in terms of procedures but often involve using high end equipment which requires significant financial investment and specially trained personnel (e.g. high speed DNA sequencing). Yet some methodologies are easy to grasp but the time needed to conduct identification is too long and commercially unrealistic and thus virtually unusable. Yet further, some methodologies are not able to distinguish a specimen when the sample contains multiple sources of animal species tissues, or at least they are not able to distinguish a specimen in one experiment.

The present invention seeks to address the aforementioned issues by providing a method which endeavors to balance different factors, or at least to provide an alternative balance, and means thereof. At least the present invention seeks to provide an alternative to the public for identifying an animal species sample, and means thereof.

SUMMARY OF THE INVENTION

According to a first aspect of the present invention, there is provided a method of rapid identification of a mammalian species origin or mammalian species origins of a sample, comprising sequential steps of:

engineering DNA probes with a length from 60 to 80 bases; said engineering including identifying regions from whole region of $48^{th}$ to $705^{th}$ bp of double stranded COI gene region of a first mammalian species, yielding a first group of 60-80 bp of DNA regions, and from the first group of 60-80 bp of DNA regions, identifying a second group of 60-80 bp DNA regions representing single-stranded sequences meeting a combination of the following criteria:
1. with a GC content 50 to 52%;
2. with a positive value of delta G at a given temperature, wherein the given temperature is a hybridization temperature ($T_{hyb}$) of 15-25° C. below a melting temperature ($T_m$), wherein the hybridization temperature ($T_{hyb}$) is a temperature at which the DNA probes hybridize during identification, and wherein the melting temperature ($T_m$) is a temperature at which the double stranded sequence at a region corresponding to the second group of the 60-80 DNA regions dissociates; and
3. in which difference between the number of secondary structures (SS) or one of the DNA regions in the second group and the value of secondary structure (SS) of the same DNA region is between 0 to 4, thus yielding a third group of DNA regions, wherein the value of the secondary structure is determined based on propensity of a base of single-stranded DNA molecules;

producing the DNA probes based on sequences of the third group of DNA regions, wherein the sequences of the DNA probes are comprised in the group consisting of SEQ ID NOs. 1-241;
collecting the sample;
processing the sample;
dividing the sample into a number of portions for situation in a multi-well container or containers;
providing the produced DNA probes from step b), wherein the number of the sample portions is greater than the number of mammalian species types from which the DNA probes derive;
selecting some or all of the DNA probes, and allocating the selected DNA probes in the multi-well container or the containers, such that each of the selected DNA probes is situated separately, for hybridization with the sample portions, respectively;
contacting the sample portions for intended hybridization with the selected DNA probes simultaneously;
analyzing the sample portions contained in the multi-well container or containers for a positive hybridization results following the contacting step; and
determining the mammalian species origin or origins of the sample according to positive hybridization results.

Preferably, the method may allow the hybridization to occur in a medium with a salt concentration of 50 mmole. The salt may be sodium chloride. The medium may be free of organic solvent.

The species may include *Bos Taurus* (cattle), *Sus scrofa* (pig), *Ovis aries* (sheep), *Equus caballus* (horse), *Canis lupus* (dog) and *Mus musculus* (mouse) and *Felis Catus* (cat).

BRIEF DESCRIPTION OF DRAWINGS

Some embodiments of the present invention will now be explained, with reference to the accompanied drawings, in which:

FIG. 2 is a key showing the pattern of distribution of species specific probes immobilized on the membranes used in experiments, results of which are demonstrated in FIG. 1 and FIGS. 3a to 3d;

FIG. 4 is a key showing the pattern of distribution of species specific probes immobilized on the membrane for multiple species detection in an experiment, results of which are demonstrated in FIG. 5.

DETAILED DESCRIPTION OF PREFERRED EMBODIMENTS OF THE INVENTION

Figure 1:
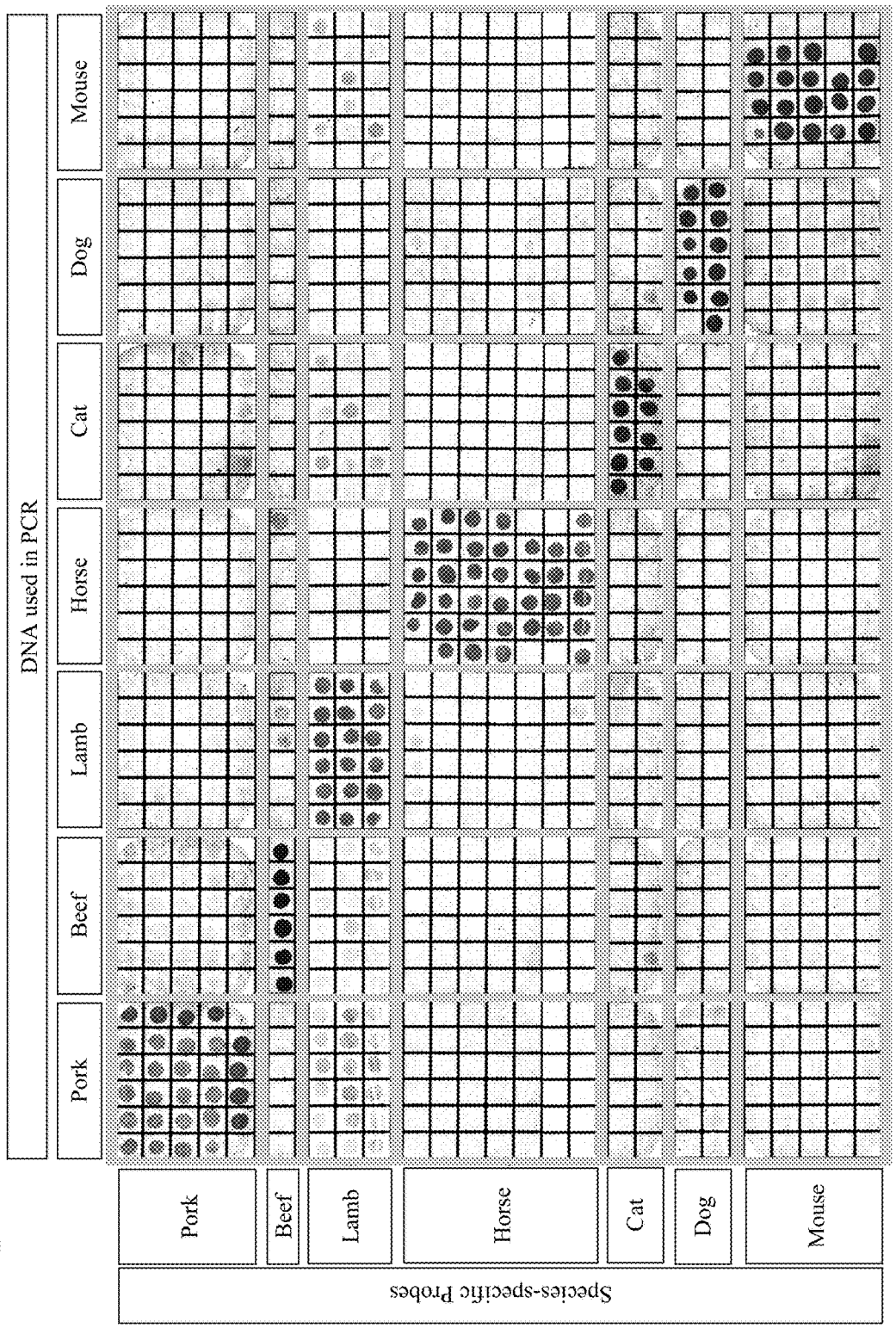
FIG. 1 shows images illustrating specificity examination of species-specific probes of each listed mammal species according to an embodiment of the present invention.

DNA probes or DNA oligo-nucleotides (or oligo-nucleotide sequences) have been widely used for a vast range of applications. The requirements for a DNA probe or a group of DNA probes suitable for use in different applications are rather different and unpredictable. The usefulness, accuracy and/or efficiency of the applications largely depend on the DNA probe sequence(s). While there has been numerous proposal of making or using DNA probes in different scenario, there is however, no one single principle that can be appropriate for use in all applications. In this context, after much research and development, a number of DNA probes have been engineered, allowing identification of mammalian species including Bos Taurus (cattle), Sus scrofa (pig), Ovis aries (sheep), Equus caballus (horse), Canis lupus (dog) and Mus musculus (mouse) and Felis Catus (cat). Accordingly, in an embodiment of the present invention, there is provided a plurality of DNA probes having DNA sequences with SEQ ID NOs. 1-241, as shown in Appendix and the Sequence Listing submitted with this patent specification. It is to be noted that the Appendix shows sequences generally mirroring those in the Sequence Listing although in the Appendix further designations are provided for reference and illustration purposes. Studies have shown that in the context of the present invention these particular sequences are on one hand sufficiently species specific and are able to reliably detect the relevant species origin of a sample or multiple species origins of a sample, as the case may be, and on the other hand they would not yield false hybridization results. Studies have also shown that sequences having at least 98% sequence identify will likewise produce workable results.

One object of this present invention is to allow rapid identification of a mammalian species origin or a mammalian species origin in one experiment or simultaneously, and efficiently, without having to make use of costly equipment.

In one embodiment of the present invention there is provided a method of rapid identification of a mammalian species origin or mammalian species origins of a sample, comprising sequential steps of:
engineering DNA probes with a length from 60 to 80 bases; said engineering including identifying regions from whole region of $48^{th}$ to $705^{th}$ bp of double stranded COI gene region of a first mammalian species, yielding a first group of 60-80 bp of DNA regions, and from the first group of 60-80 bp of DNA regions, identifying a second group of 60-80 bp DNA regions representing single-stranded sequences meeting a combination of the following criteria:

1) with a GC content 50 to 52%;
2) with a positive value of delta G at a given temperature, wherein the given temperature is a hybridization temperature ($T_{hyb}$) of 15-25° C. below a melting temperature ($T_m$), wherein the hybridization temperature ($T_{hyb}$) is a temperature at which the DNA probes hybridize during identification, and wherein the melting temperature ($T_m$) is a temperature at which the double stranded sequence at a region corresponding to the second group of the 60-80 DNA regions dissociates; and
3) in which difference between the number of secondary structures (SS) and one of the DNA regions in the second group and the value of secondary structure (SS) of the same DNA region is between 0 to 4, thus yielding a third group of DNA regions, wherein the value of the secondary structure is determined based on propensity of a base of single-stranded DNA molecules;

producing the DNA probes based on sequences of the third group of DNA regions, wherein the sequences of the DNA probes are comprised in the group consisting of SEQ ID NOS. 1-241;
collecting the sample;
processing the sample;
dividing the sample into a number of portions for situation in a multi-well container or containers;
providing the produced DNA probes from step b), wherein the number of the sample portions is greater than the number of mammalian species types from which the DNA probes derive;
selecting some or all of the DNA probes, and allocating the selected DNA probes in the multi-well container or the containers, such that each of the selected DNA probes is situated separately, for hybridization with the sample portions, respectively;
contacting the sample portions for intended hybridization with the selected DNA probes simultaneously;
analyzing the sample portions contained in the multi-well container or containers for a positive hybridization results following the contacting step; and
determining the mammalian species origin or origins of the sample according to positive hybridization results.

Accordingly, a skilled person would be able to conduct one experiment for detecting the species origin of a sample. For example, each reaction chamber in multi-well containers receives a sample portion possibly from one or more species. The sample portion may be derived from animal tissues. The sample portions are subjected to hybridization with the selected DNA probes simultaneously. By "subjecting the sample portions to hybridization with the selected DNA probes simultaneously", it refers to, in one embodiment, that each of the chambers receiving only one of the selected DNA probes. In such embodiment, when there is positive hybridization result in the one chamber, this result is indicative of the sample portion in that chamber containing the animal issue from which that DNA probe derives. Since there are multiple chambers in the multi-well container, multiple hybridizations can occur simultaneously in one experiment. It can thus be envisaged that if a sample contains tissues from multiple animal species, and there is provided with DNA probes corresponding to these animal species, the present invention can allow detection of all the animal species origins to the extent the DNA probes encompass. This translates to efficiency in species origin identification, or rapid identification of species origin(s).

In a specific example, if there is only one species origin, e.g. cattle, of the sample, then positive hybridization results will be detected from the hybridization(s) in which the DNA probe(s) is(are) designed from the DNA sequence of that particular species, i.e. cattle. On the other hand, if there are two species origins, e.g. cattle and pig, then positive hybridization results will be detected from the hybridizations in which the DNA probes are designed from the DNA sequences of both the species of cattle and pig. This provides a technical advantage of allowing rapid identification of multiple species origins in one step. In other words, the present invention allows identification of mammalian species in a mixed population of samples within a single experiment.

As explained above, the usefulness of DNA probes will depend on the particular sequences thereof. One aspect of the present invention provides a method of engineering DNA probes for use in identification, but in the context of rapid identification of a mammalian species origin or mammalian species origins as explained above. More detailed procedures for designing these DNA probes are described as follows.

The DNA sequences used to define those probes are required to possess sufficient differences to distinguish different species. In one embodiment, the COI gene of a number of mammalian species is utilized. Specifically, studies leading to the present invention have shown that $48^{th}$ to $705^{th}$ bp region of this gene is particularly suitable to be used as the DNA barcode for species identification in animals. The region can be amplified by PCR with the use of universal primers cocktail, making it available to generate a large amount of amplicons for hybridization for identification. Embodiments of the present invention will thus make use of this region.

Apart from the region of DNA sequence, to design species-specific DNA probes which are able to be used in a single experiment for identifying multiple species, the inventors of the present invention have determined that the probes should have highly similar physical and chemical properties for hybridization at the same environmental conditions. Moreover, other criteria are also required to maximize the specificity, and reliable, of the probes. Therefore, in the present invention, criteria concerned for defining suitable DNA probes include the length, guanine-cytosine (GC) content, delta G, melting temperature and hybridization temperature, and presence of secondary structure.

There is however priority in these criteria when designing the probes. Length is the first concerned criterion. In theory, and typically, longer probes would give higher specificity and more efficient during hybridization. However, conventional, longer probes were seen as undesirable because they were more difficult to generate, and their structures, and thus binding behavior, are more unpredictable. For example, synthesizing longer oligonucleotides would often require enzymatic ligation approach which is more complicated and costly, rendering synthesis of longer probes commercially not possible in companies with less financial resources. Setting aside issues of cost, cross hybridization is also related to the longer length oligonucleotides and is not desirable. Accordingly, many probes that were suggested in the prior art were rather short. On the other hand, shorter probes are easier to generate.

Studies leading to the invention of the present context have identified that probes with a length from 50-80 bp are generally able to achieve the identification desired in the context of the present invention satisfactorily. The studies have shown that probes with this length (longer than most probes previously suggested), in the context of the other criteria as explained below, still provide the ability to distinguish species effectively and reliably. In a more specific embodiment, the length of the probes is from 60-80 bp. Studies have shown that the present invention have defined desired probes within the DNA barcode region with lengths at, for example, 60, 70 and 80 bp for the mammalian species in Table 1. It is to be understood that in the context of the present invention, the probes with a length from 60-80 bp all satisfy the length criterion.

The next criterion is GC content of the probe, i.e. the percentage of guanine and cytosine of the nitrogenous bases, in the probe. The requirement on GC content differs, depending on the particular application. There are four different nitrogenous bases in DNA, including guanine (G), cytosine (C), adenine (A) and thymine (T). This might be due to the fact that G and C bind each other by forming 3 hydrogen bonds while A and T form 2 hydrogen bonds, making a DNA probe with higher GC content more stable, or there could be other reasons. As a result, in the scenario in which a probe with a higher GC content is used, a higher melting temperature (Tm) so as to provide enough energy for denaturing the DNA sequences to which the probe would bind would be used. It follows that a higher hybridization temperature ($T_{hyb}$) for the DNA sequences is also resulted. While a higher GC content would increase the specificity in hybridization between oligonucleotide probe and complementary DNA, it does not mean DNA probes with the highest GC content would be suitable in the context of the present invention. Studies leading to the present inventions show that if the GC content is too high, the sequence of the DNA probes could become undesirably coiled. Further, the criterion is not a standalone requirement of the GC content, but also the melting temperature and hybridization temperature used, in the context of other criteria discussed above and below. In any event, according to the present invention, with respect to the above listed mammalian species, probes with a GC content between 50% and 52% is appropriate from the perspective of both accuracy and reliability.

The third criterion is delta G of the probes. Delta G is the change in Gibbs free energy (in units of kcal/mole) between a system and the environment. In the context of DNA or oligonucleotide sequence, when there are two complementary strands, they have a tendency to form a duplex structure. A positive delta G at a given temperature indicates that the two strands tend to keep in single-stranded status while a negative delta G indicates that the two stands tend to bind together to form a double-stranded structure. Studies leading to the present invention indicate that probes a positive delta G, in the context of other criteria, are desired. DNA probes with a delta G value of more than 1 is advantageous. Meeting these requirements, formation of hairpin structures due to self-binding of short complementary sequences within the probe sequence would be minimized. It is to be noted that while conceivably there could be other combinations of criteria which would work in achieving the engineering of probes (e.g. when the delta G value is not positive), the present invention is concerned with a combination of a subset of specific criteria that together have been shown to work.

The next criterion includes the conditions of melting temperature ($T_m$) and hybridization temperature ($T_{hyb}$). These two conditions are inter-related. (By "hybridization temperature ($T_{hyb}$)", it refers to a temperature at which the designed probes hybridize with the DNA sequences of a sample during an identification exercise. By "melting temperature ($T_m$)", it refers to a temperature at which a double stranded DNA of a region of a gene in the sample dissociates into two single strands. The sequence of the designed probes corresponds to the sequence of the respective region of the double stranded DNA. In the context of this invention, the melting temperature ($T_m$) is used as a reference temperature when the hybridization temperature ($T_{hyb}$) is discussed.) It has been shown that at $T_m$, 50% of DNA exists in single-stranded status, determined mathematically or by computer simulation. Generally, the equation derived by thermodynamic basis sets for nearest neighbor interactions is commonly used. On the other hand, hybridization conditions are selected to favor the formation of DNA-probe duplex. Usually, or at least in this embodiment of the present invention, the hybridization temperature ($T_{hyb}$) is as much as 25° C. below the melting temperature ($T_m$), hence allowing the defined probes to bind to their complementary region on the amplicons. Moreover, the meting temperature ($T_m$) is related to and greatly affected by the GC content, length of the sequence and chemistry conditions, such as salt concentration and presence of organic solvents. Accordingly, in the context of this embodiment the hybridization temperature ($T_{hyb}$) substantially 25° C. below the melting temperature ($T_m$) is appropriate in allowing and enhancing the hybridization, and thus identification. However, studies have shown that, advantageously, the hybridization temperature ($T_{hyb}$) may be from 15-25° C. below the melting temperature ($T_m$). The melting temperature ($T_m$) for the probes with GC content at 50% to 52% is between 79° C. to 83° C. Together with the criterion of delta G, the calculated hybridization temperature ($T_{hyb}$) of the defined probes require above theoretical calculated temperature of 60° C. with 50 mmole of a salt, e.g. sodium chloride, and without any organic solvent.

Another criterion concerned is the presence of secondary structure (SS) in the DNA probes. In single-stranded DNA, SS referred to the structures, hairpins as mentioned in the previous section, formed by self-binding of short complementary sequences within the probe. On one hand, the SS allows the single-stranded DNA to exist in a more stable form (at lower free energy condition). However, secondary structures occurred in oligonucleotide probes will impair the hybridization performance of the probes by reducing binding efficiency and increasing probe to probe variability. Reference is made to Armitage et al, 2001, Armitage et al 2003, Ramdas et al 2004, and Chou et al 2004. SS of a given single stranded DNA can be calculated and represented in SS value and number of SS. Probes with a SS value close to the number of SS indicates that there is a higher propensity for a nitrogenous base in the probe to be single stranded in all predicted SS. In other words, the value of the secondary structure is determined based on at least the propensity of a base of single-stranded DNA molecules.

Under desired temperature and environmental conditions, such as concentration of salts, a given probe or single-stranded DNA with one or more secondary structures is formed. The exact number of secondary structures can be determined by conventional mathematical calculation or simulation, with the aid of many computational programs. While the present invention is about this calculation or simulation, it is to be noted that a person in the art is be aware that, for example, the program Mfold, may be used in ascertaining secondary structure including secondary structure value and secondary structure number. Reference is made to Zuker et al 2003. The number of times that a base is single stranded in the computed foldings is called a "secondary-structure count" or "ss-count" number. The average of the ss-count of each base of a given single stranded DNA is the SS value. An oligonucleotide or single stranded DNA with a SS value closed to the number of secondary structures (difference between SS value and number of secondary structures) indicates that there is a higher propensity for a nitrogenous base in the oligonucleotide to be single-stranded in all predicted secondary structures.

The mathematical calculation or simulation is derived from the energy rules developed by Turner. In this connection, reference is made to Jaeger, Turner, and Zuker (Proc. Natl. Acad. Sci. USA, 86, 7706-7710 (1989). While the present invention is not concerned with the design of the simulation for use in determining the secondary structure, it is worth mentioning that Turner and his colleagues sought to determine optimal and suboptimal secondary structures of a RNA molecule. The general algorithm for determining multiple optimal and suboptimal secondary structures is described by the Dr. Michael Zuker who design the program. Reference is made to Science 244, 48-52 (1989). A skilled person in the art would use such tools widely accepted in the field in determining secondary structure, secondary structure value and secondary structure number.

In the present invention, studies have shown that the desired difference between the number of secondary structures (SS) and the value of secondary structure (SS) should be between 0 to 4. Preferably, the probes with smallest number of SS and SS value closest to the number of SS are taken into account.

TABLE 1

List of targeted species for defining species specific probes in the present invention

| Common Name | Scientific Name |
| --- | --- |
| Cattle | Bos taurus |
| Pig | Sus scrofa |
| Sheep | Ovis aries |
| Horse | Equus caballus |
| Dog | Canis lupus |
| Mouse | Mus musculus |

COI gene sequences data, including all full, partial and fragment sequences, of the targeted species can be obtained from GenBank and BOLD databases. When designing the DNA probes, duplicated sequence records between these two databases were removed. After alignment, the $48^{th}$ to $705^{th}$ bp fragment from 5' end of each record was extracted. For those species with reference sequence in GenBank database, that particular sequence was used as the template to define the species-specific probes. For those species without reference sequences in GenBank database, the most populated sequence in that species was used as the template to define the probes.

The GC content and $T_m$ of all possible sequences with length of 60, 70 and 80 bp from the obtained template sequences were calculated. Those sequences with GC content between 50% and 52% were picked for next step. All delta Gs at 25° C. and 65° C. of these picked sequences were calculated with the use of online program, ZIPFOLD, DINAMELT server, although, as explained above, any other suitable available tools in the market may be used. Delta G value at 25° C. and 65° C. larger than −4 kcal/mol and 1 kcal/mol respectively were selected for further step. At the 3' end, if sequences contained 3 or more contiguous G or C nucleotide within the last 5 nucleotides, those sequences were discarded. Selected sequences were then passed to another online program, DNA-folding form, The Mfold web server for calculating the SS value and predicting the secondary structures at 25° C. and 65° C. Those sequences with standard deviation smaller than 1 in the SS value and the number of secondary structure smaller than 3 were selected. If no sequence fulfilled these criteria, those DNA sequences with values closest to these two criteria could be accepted.

After passing the selection with those physical criteria, the specificity of these selected sequences was verified within species and with other species. For intraspecific comparison, the selected sequences were compared with all COI genes of the same species obtained. Any different sequences found were also picked to undergo interspecific comparison. In such situation, a group of probes was defined for identifying that target species. If no difference was found, the sequences can be passed directly to interspecific comparison which was carried out by the BLAST system with GenBank database. In interspecific comparison, results are sorted according to the identity. Sequences that showed any result with identity higher than 97% to other species would not be used as species-specific probes.

Similar procedures described above can be applied for defining species specific probes for other organisms.

In order to appreciate the above novel method for rapid identification of a mammalian species origin or mammalian species origins, the present invention is to be contrasted with two main conventional approaches, as follows.

(a) DNA Fingerprinting by Restriction Fragment Length Polymorphism (RFLP)

This method was first introduced in 1985 for human identification and was subsequently applied to identification of other organisms. PCR amplification of short tandem repeat (STR) and variable number of tandem repeats (VNTR) had developed to improve the method. Endonucleases are used to cut the specific restriction sites on the PCR amplified amplicons, generating a number of small fragments at different sizes. The species specific pattern of different fragments can be observed on agarose gel after electrophoresis or DNA chips. These two detection methods had already applied to identify fish species. The problem is that with this approach, sophisticated procedure or expensive equipment is required, such as southern blotting or DNA chip analyzing machine. Moreover, incomplete digestion may occur and intraspecific variations could alter the number of restriction sites on the sequence. Besides, if the sample contained different species, RFLP cannot distinguish all species within one experiment since the fragment pattern generated is combined by several species specific patterns. Multiple experiment or further analysis to resolve the merged patterns is required.

(b) DNA Sequencing

Due to the accumulation of mutation in the genome, particular genes or DNA regions have enough differences to serve as a marker for species identification. The differences can be notified by sequencing and comparing the target DNA region in different species. With PCR amplification technique, the PCR-sequencing method, which now is recognized as DNA-barcoding, has been applied in species identification for several years. A 658 base pairs (bp) sequence in mitochondrial gene, cytochrome c oxidase I (COI), have examined extensively to identify wild range of animal taxa, including insects, aquatic animals, and birds. U.S. Food and Drug Administration accepted COI-based barcoding as one of the species identification methods for fish. A standard operating procedure (SOP) had been published by FDA after a formal single laboratory validation at Center for Food Safety and Applied Nutrition (CFSAN), FDA). This SOP is intended to replace the LIB No. 4420 now. This conventional DNA barcoding method requires analyzing the sequence of whole barcode. Its application is limited by high operational cost due to the requirement of equipment and time for data analysis. Furthermore, additional costs and steps are required after PCR amplification if samples containing multiple species are examining. PCR amplified amplicons with different species cannot be sequenced in a single experiment. Amplicon separation of different species by bacterial cloning is required. Processes involve ligation, transformation, culture of bacterial colonies on agar plate. Extra step, including picking bacterial colonies, culture of bacterial in broth or even prepping the amplicon ligated plasmids is required if the biotechnology company have not provide those services. It will further increase 2 more days in overall process.

In view of the conventional approaches, and to decrease the cost and shorten the time for species identification, and to further allow the identification of multiple species within one experiment, new identification approach is required. The present invention, as illustrated above, defines species specific DNA sequences served as DNA probes for identifying multiple species in the same experiment through DNA hybridization. The target species involved in the present invention are mammalian species, including *Bos taurus, Sus scrofa, Ovis aries, Equus caballus, Canis lupus* and *Mus musculus*.

It is to be noted that more than one probe may be needed to ascertain whether a sample originates from a particular inter-species or not. This is because in certain region of the COI gene of a particular inter-species, the sequence thereof may differ among intra-species of that particular inter-species. To assess whether the sample originates from the inter-species or not, multiple probes derived from different intra-sequences of all of the known intra-species would be needed. For example, probes with SEQ ID NOs. 7-11 shown in Appendix are all derived from different intra-species of the same inter-species. Accordingly, it is envisaged that the present invention would be capable of detecting not only the inter-species origin(s) of a sample, but also the intra-species origin(s) of a sample.

In order to more clearly illustrate the present invention, the following, with reference to the figures, will demonstrate the elements of the present invention by way of example.

A first experiment was conduct to test whether the engineered DNA probes were able to identify mammalian species samples with sufficient species specificity. In this experiment, the DNA used in each PCR is isolated or originates from a single species. PCR amplicons of each species were hybridized to all probes as indicated in FIG. 1. Hybridization temperature during the experiment was 42° C. 10 min color development for signal detection was applied. Signal was detected after hybridization between species-specific probes.

A number of observations can be seen from FIG. 1. Please however also refer to FIG. 2, FIG. 6 and the Sequence Listing. Specifically, FIG. 2 is a key showing which probes are located in which wells on the templates. The probes were immobilized on the membranes used in the experiments, results of which are shown in FIG. 1, and FIGS. 3a to 3d. The following is also to be noted.

Ss: *Sus scrofa* (Pork)
Bt: *Bos taurus* (Beef)
Oa: *Ovis aries* (Lamb)
Ec: *Equus caballus* (Horse)

Cl: *Canis lupus* (Dog)
Fc: *Felis catus* (Cat)
Mm: *Mus musculus* (Mouse)

For beef, probe P6 showed weak non-specific binding with *Ovis aries* (lamb) and *Equus caballus* (horse).

For pork, weak non-specific binding signal to *Bos taurus* (beef) was found in some probes. Non-specific binding signal to *Felis catus* (cat) were also found in probe P10a (60 bp), and probe P5a and P6a (70 bp).

For horse, Probes P1 to P4 showed weak non-specific signal against *Ovis aries* (lamb) and *Canis lupus* (dog).

70 bp Weak non-specific binding signal were observed in P14 and P15 against *Canis lupus*.

For cat, only probe P6 with 60 bp in length showed non-specific binding with *Bos taurus*.

For dog, All probes are specific to *Canis lupus*.

For mouse, All probes were specific to *Mus musculus* (mouse). Weak non-specific binding signal were found in probes with 70 bp length, P3 and P4, against *Canis lupus*.

For lamb, Probes P4a-4d, P5d, P6a-d and P7d in 60 bp length showed non-specific binding signal to *Sus scrofa* (pork). Probes P4b, P5b, P6b and P7b also showed non-specific binding signal to *Felis catus* and *Mus musculus*.

In another series of experiments, temperature for hybridization and time for hybridization for the identification of the species using the probes were studied.

Figure 3A:
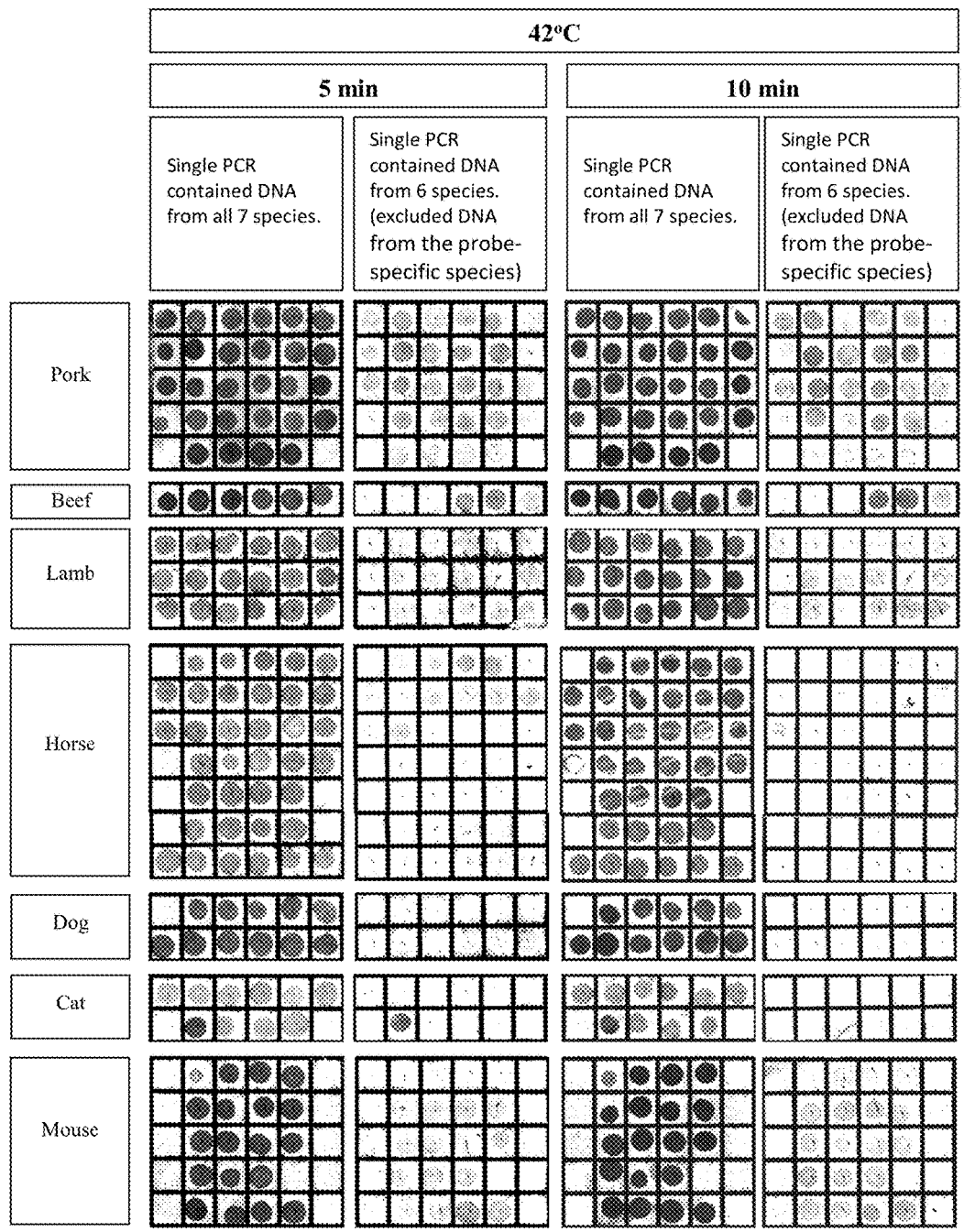
FIGS. 3a to 3d show the effect of hybridization temperature and/or time for hybridization according to an embodiment of the present invention.

In FIG. 3a, it is shown that the temperature for hybridization was at 42° C. Some non-specific signal was found in pork, beef, horse, cat and mouse specific probes. However, at least 2 to 3 probes in each species were specific enough at these hybridization conditions. Stronger signal was found when color development time was increased from 5 min to 10 min.

Figure 3B:
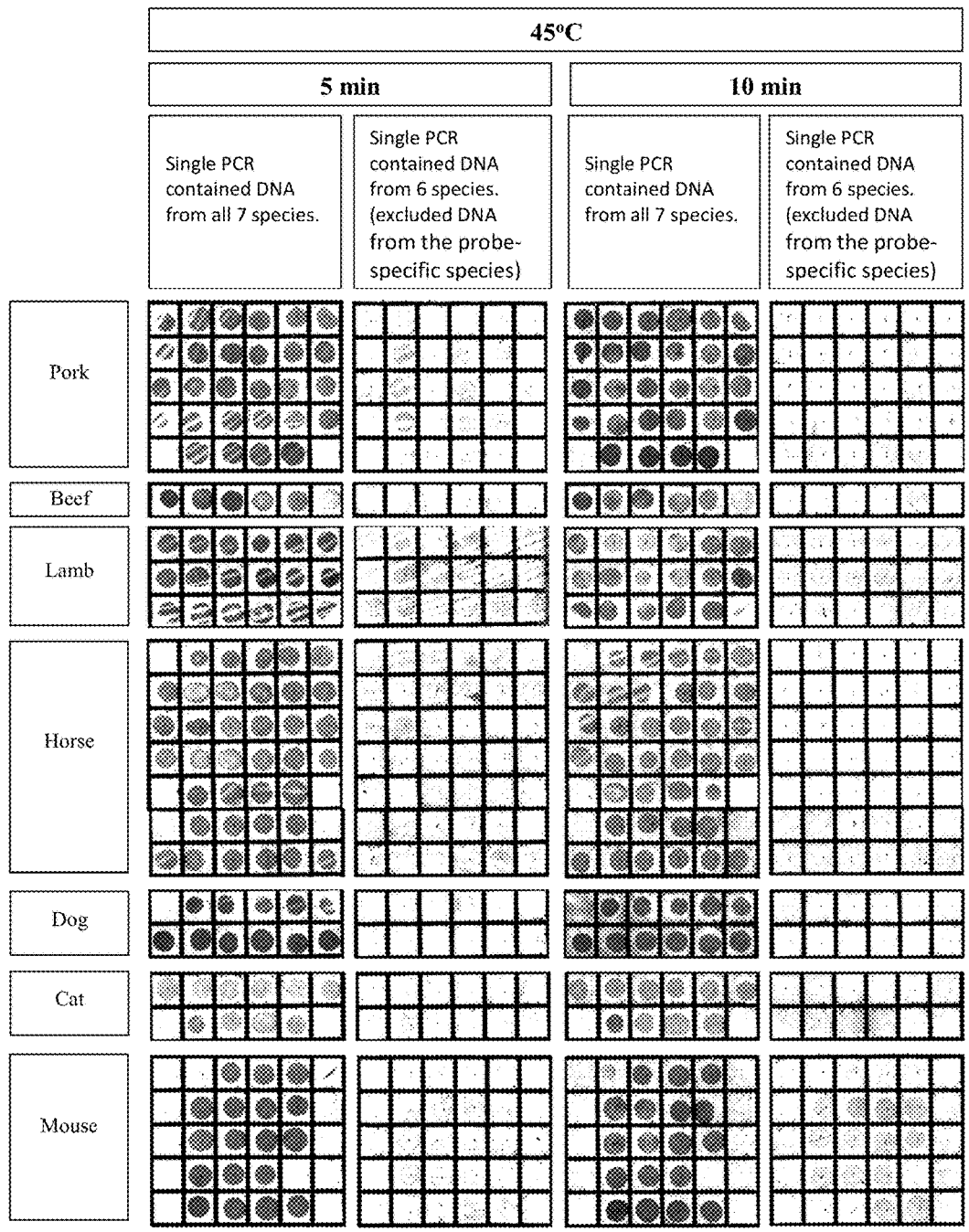

In FIG. 3b, the temperature for hybridization was increased from 42° C. to 45° C. Signal had become more specific. Nearly all probes were specific at 5 min color development time. Stronger signal were found when color development (hybridization) time was increased from 5 min to 10 min, but some non-specific signals were found in several mouse specific probes.

Figure 3C:
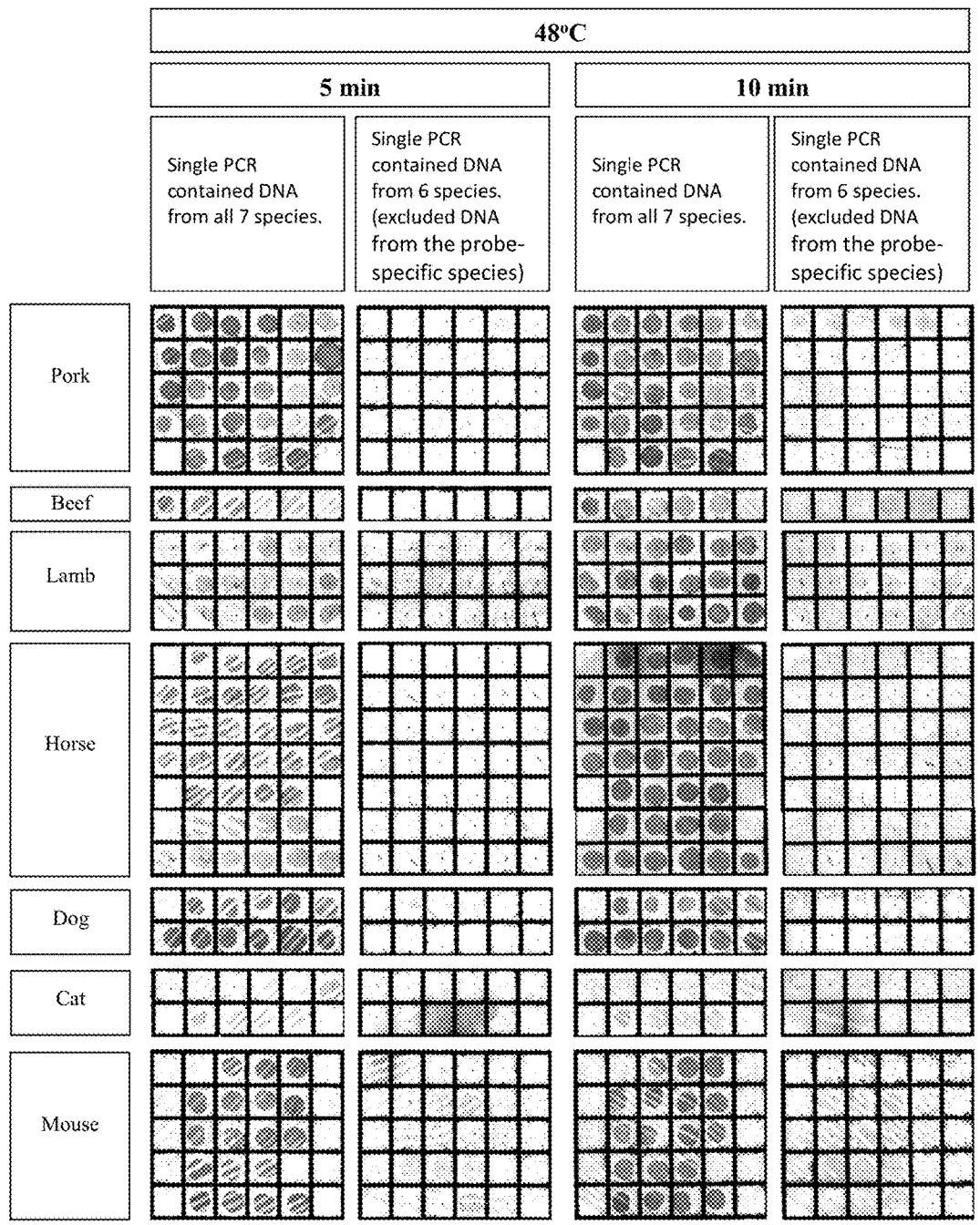

In FIG. 3c, signal became weaker when temperature was increased to 48° C. The cat specific probes nearly gave no signal. Apart from the cat specific probes, strong and specific signals were found in other species when color development time was increased to 10 min.

Figure 3D:
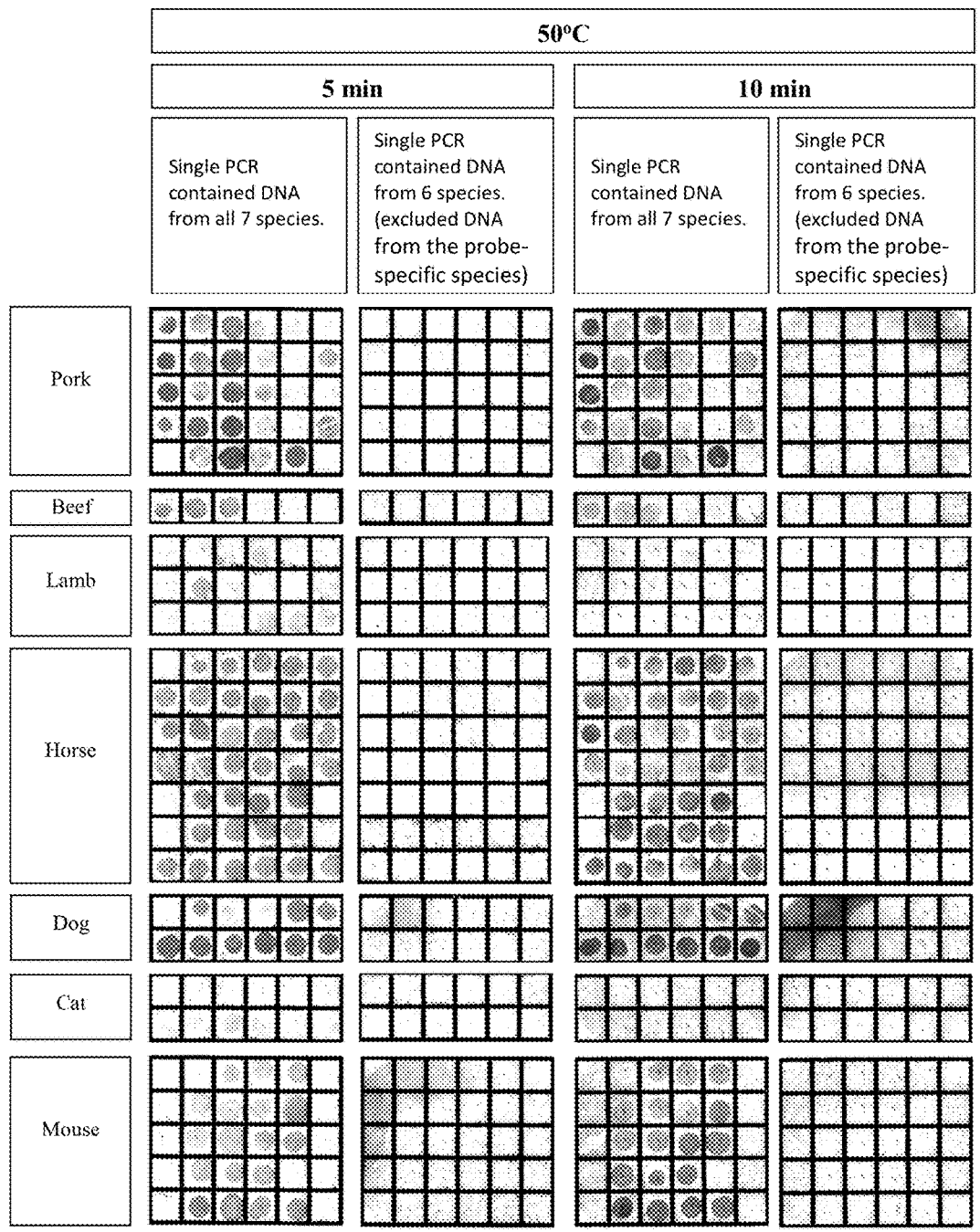

In FIG. 3d, signal became weak at 50° C. Nearly no signal could be detected for lamb and cat specific probes. However, most probes for pork, beef, horse, dog and mouse still gave specific signal.

In the experiments as shown in FIGS. 3a to 3d, it can be seen that the specific engineered probes are specific enough, although the working temperature for each species for optimal identification may vary. From all hybridization conditions, the hybridization temperature of about 45° C. yields better specific signal for all species. Several probes can be selected at this condition and place in the same membrane for a multi-species detection. The duration for color development is between about 5 to 10 min.

Figure 5:
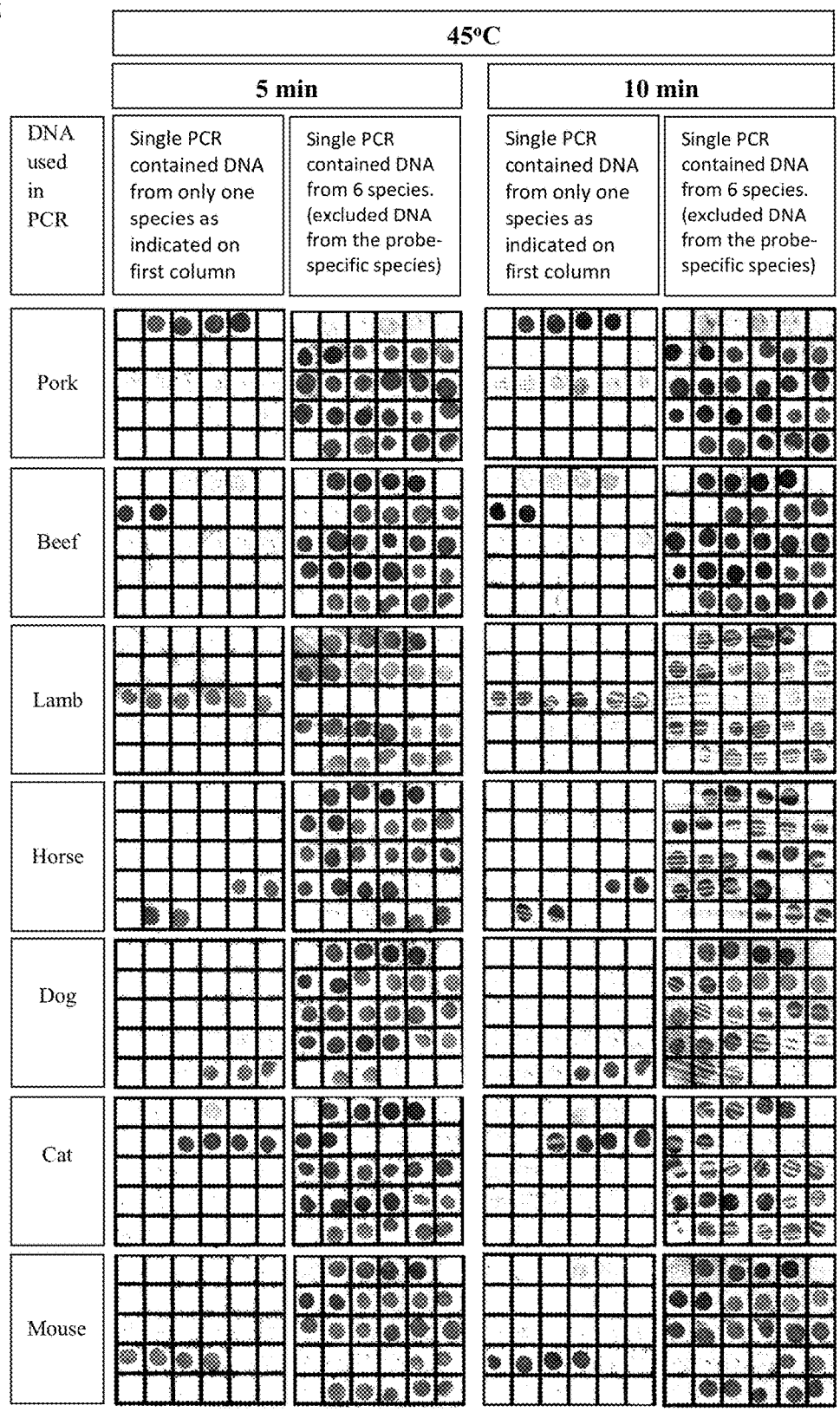
FIG. 5 shows the effect of multiple species detection according to an embodiment of the present invention.

In another experiment, it is shown that the present invention can be applied for multiple species detection simultaneously. Referring to FIG. 5, there is shown a panel of species specific probes selected from each mammal species that are immobilized on the same membrane for multiple species detection. Please refer to FIG. 2 for the locations of the different probes in the panel.

Specific probes from each species were selected and immobilized on same membrane. The specificity of these probes in mixed samples was examined. For 5 min color development (hybridization time), it is shown that the engineered probes are specific to their own species. No non-specific signals were found when hybridized with PCR product amplified from DNA of other species. For 10 min of color development, signal was stronger but some non-specific signals were found although the identification was still satisfactory.

It is to be noted that the following a skilled person in the art possess the skills disclosed in the following reference, which are incorporated in this description in their entirety.

1. Gill, P., Jeffreys, A. J. and Werrett, D. J., (1985), Forensic application of DNA 'fingerprints'. *Nature*, 12-18; 318 (6046): p 577-579.
2. Lockley, A. K. and Bardsley, R. G., (2000), DNA-based methods for food authentication. *Trends in Food Science and Technology*, 11, p 67-77.
3. Handy, S. M., Deeds, J. R., Ivanova, N. V., Hebert, P. D. N., Hanner, R., Ormos, A., Weigt, L. A., Moore, M. M. and Yancy, H. F. (2011). A single laboratory validated method for the generation of DNA barcodes for the identification of fish for regulatory compliance. *Journal of AOAC International*. 94 (1), 201-210.
4. Meusnier, I., Singer, G. A., Landry, J. F., Hickey, D. A., Hebert, P. D. and Hajibabaei, M., (2011), A universal DNA mini-barcode for biodiversity analysis, *BMC Genomics*, 9, p 214.
5. Shokralla, S., Zhou, X., Janzen, D. H., Hallwachs, W., Landry, J. F., Jacobus, L. M. and Hajibabaei, M., (2011), Pyrosequencing for mini-barcoding of fresh and old museum specimens, *PLoS One*, 6(7):e21252, Epub 2011 Jul. 27.
6. Chou, C. C., Chen, C. H., Lee, T. T. and Peck, K., (2004), Optimization of probe length and the number of probes per gene for optimal microarray analysis of gene expression, *Nucleic Acids Research*, 32(12), e99.
7. Aquino de Muro, M., (2008), Probe Design, Production, and Applications, *Molecular Biomethods Handbook*, A, p 41-53.
8. Armitage, B. A., (2001), Effect of secondary structure on the thermodynamics and kinetics of DNA hybridization to DNA hairpins, *Journal of the American Chemical Society*, 123, p 10805-10813
9. Armitage, B. A., (2003), The impact of nucleic acid secondary structure on DNA hybridization. *Drug Discovery Today*, 8, p 222-228.
10. Ramdas, L., Cogdell, D. E., Jia, J. Y., Taylor, E. E., Dunmire, V. R., Hu, L., Hamilton, S. R. and Zhang, W., (2004), Improving signal intensities for genes with low-expression on oligonucleotide microarrays, *BMC Genomics*, 5(1), p 35-44.
11. Zuker et al, (2003), Mfold web server for nucleic acid folding and hybridization prediction, Nucleic Acids Research, Vol. 31, No. 13, 2003.
12. Jaeger, Turner, and Zuker, (1989), *Proc. Natl. Acad. Sci. USA*, 86, 7706-7710.
13. Zuker et al, (1989), *Science* 244, 48-52.
14. SantaLucia, Jr (1998), A unified view of polymer, dumbbell, and oligonucleotide DNA nearest-neighbor thermodynamics. *Proc. Natl. Acad. Sci. USA* 95, 1460-1465.
15. Peyret, N. (2000), Prediction of Nucleic Acid Hybridization: *Parameters and Algorithms PhD dissertation*, Wayne State University, Department of Chemistry, Detroit, Mich.

It should be understood that the above only describes the preferred embodiments according to the present invention, and that modifications and alterations may be made thereto without departing from the spirit of the invention.

APPENDIX

Key-Species codes:
*Bos tarrus*-B
*Sus scrofa*-S
*Ovis Aries*-O
*Equus caballus*-E
*Canis lupus*-C
*Mus musculus*-M
*Felis catus*-F

| SEQ ID NO. | Species code | Designation | Sequence |
|---|---|---|---|
| 1 | B | P1 | TCCGTAATAATTACCGCCGTACTACTACTACTCTCGCTCCCTGTATTAGCAGCCGGCATC |
| 2 | B | P2 | CCGTAATAATTACCGCCGTACTACTACTACTCTCGCTCCCTGTATTAGCAGCCGGCATCA |
| 3 | B | P3 | CGTAATAATTACCGCCGTACTACTACTACTCTCGCTCCCTGTATTAGCAGCCGGCATCAC |
| 4 | B | P6a | CCGGAACCTAAATACAACCTTCTTCGACCCGGCAGGAGGAGGAGACCCTATTCTATATCA |
| 5 | B | P6b | CCGAAACCTAAATACAACCTTCTTCGACCCGGCAGGAGGAGGAGACCCTATTCTATATCA |
| 6 | B | P6c | CCGGAACCTAAATACAACTTTCTTCGACCCGGCAGGAGGAGGAGATCCTATTCTATACCA |
| 7 | S | P4a | AGCCTACTAATTCGCGCTGAACTAGGTCAGCCCGGAACCCTACTTGGCGATGATCAAATC |
| 8 | S | P4b | AGCCTACTAATTCGCGCTGAACTAGGTCAGCCCGGAACTCTACTTGGCGATGATCAAATC |
| 9 | S | P4c | AGCCTGCTAATTCGCGCTGAACTAGGTCAGCCCGGAACCCTACTTGGCGATGATCAAATC |
| 10 | S | P4d | AGCCTACTAATTCGCGCTGAACTAGGTCAGCCCGGAACCCTACTTCCCCATGATCAAATC |
| 11 | S | P4e | AGCCTACTAATTCGCGCTGAACTAGGTCAGCCCGGAACTTTACTTGGCGATGACCAAATC |
| 12 | S | P5a | TTGAGCCTACTAATTCGCGCTGAACTAGGTCAGCCCGGAACCCTACTTGGCGATGATCAA |
| 13 | S | P5b | TTGAGCCTACTAATTCGCGCTGAACTAGGTCAGCCCGGAACTCTACTTGGCGATGATCAA |
| 14 | S | P5c | TTGAGCCTGCTAATTCGCGCTGAACTAGGTCAGCCCGGAACCCTACTTGGCGATGATCAA |
| 15 | S | P5d | TTGAGCCTACTAATTCGCGCTGAACTAGGTCAGCCCGGAACCCTACTTCCCCATGATCAA |
| 16 | S | P5e | TTAAGCCTACTAATTCGCGCTGAACTAGGTCAGCCCGGAACTTTACTTGGCGATGACCAA |
| 17 | S | P6a | TGAGCCTACTAATTCGCGCTGAACTAGGTCAGCCCGGAACCCTACTTGGCGATGATCAAA |
| 18 | S | P6b | TGAGCCTACTAATTCGCGCTGAACTAGGTCAGCCCGGAACTCTACTTGGCGATGATCAAA |
| 19 | S | P6c | TGAGCCTGCTAATTCGCGCTGAACTAGGTCAGCCCGGAACCCTACTTGGCGATGATCAAA |
| 20 | S | P6d | TGAGCCTACTAATTCGCGCTGAACTAGGTCAGCCCGGAACCCTACTTCCCCATGATCAAA |
| 21 | S | P6e | TAAGCCTACTAATTCGCGCTGAACTAGGTCAGCCCGGAACTTTACTTGGCGATGACCAAA |
| 22 | S | P7a | GAGCCTACTAATTCGCGCTGAACTAGGTCAGCCCGGAACCCTACTTGGCGATGATCAAAT |

APPENDIX-continued

Key-Species codes:
*Bos tarrus*-B
*Sus scrofa*-S
*Ovis Aries*-O
*Equus caballus*-E
*Canis lupus*-C
*Mus musculus*-M
*Felis catus*-F

| SEQ ID NO. | Species code | Designation | Sequence |
|---|---|---|---|
| 23 | S | P7b | GAGCCTACTAATTCGCGCTGAACTAGGTCAGCCCGGAACTCTACTTGGCGATGATCAAAT |
| 24 | S | P7c | GAGCCTCCTAATTCGCGCTGAACTAGGTCAGCCCGGAACCCTACTTGGCGATGATCAAAT |
| 25 | S | P7d | GAGCCTACTAATTCGCGCTGAACTAGGTCAGCCCGGAACCCTACTTCCCCATGATCAAAT |
| 26 | S | P7e | AAGCCTACTAATTCGCGCTGAACTAGGTCAGCCCGGAACTTTACTTGGCGATGACCAAAT |
| 27 | S | P9a | AAGCCGGAGCGGGTACTGGATGAACTGTATACCCACCTTTAGCTGGAAACTTAGCCCATG |
| 28 | S | P9b | AAGCCGGGGCGGGTACTGGATGAACCGTATACCCACCTTTAGCTGGAAACTTAGCCCATG |
| 29 | S |  | AAGCCGGGGCGGGTACTGGATGAACCGTATACCCACCTTTAGCCGGAAACTTAGCCCATG |
| 30 | S |  | AGGCCGGAGCGGGTACTGGATGAACTGTATACCCGCCTTTAGCTGGAAACTTAGCCCACG |
| 31 | S |  | AGGCCGGAGCGGGTACTGGATGAACTGTATACCCACCTTTAGCTGGAAACTTAGCCCACG |
| 32 | S |  | AAGCCGGAGCGGGTACTGGATGAACCGTATACCCACCTTTAGCTGGAAACTTAGCCCATG |
| 33 | S |  | AAGCCGGGGCGGGCACTGGATGAACCGTATACCCACCTTTAGCTGGAAACTTAGCCCATG |
| 34 | S |  | AAGCCGGGGCGGGTACCGGATGAACCGTATACCCACCTTTAGCTGGAAACTTAGCCCATG |
| 35 | S |  | AAGCCGGGGCGGGTACTGGATGAGCCGTATACCCACCTTTAGCTGGAAACTTAGCCCATG |
| 36 | S |  | AAGCCGGAGCGGGTACTGGATGAACCGTATACCCACCTTTAGCTGGAAACTTAGCCCATG |
| 37 | S |  | AAGCCGGGGCGGGTACTGGATGAACCGTATACCCACCTTTAGCTGGAAACTTAGCCCGTG |
| 38 | S |  | AAGCCGGAGCGGGTACTGGATGAACTGTATATCCACCTTTAGCTGGAAACTTGGCCCATG |
| 39 | S |  | AAGCCGGGGCGGGTACTGGATGAACCGAATACCCACCCTTAGCTGGAAACTTAGCCCAAG |
| 40 | S |  | AAGCCGGGGCGGGTACTGGATGAACCGTATACCCACCTTTAGCTGGAAACTTACCCCATG |
| 41 | S | P10a | GGCATCCTCAATAGTAGAAGCCGGAGCGGGTACTGGATGAACTGTATACCCACCTTTAGC |
| 42 | S | P10b | GGCATCCTCAATAGTAGAAGCCGGGGCGGGTACTGGATGAACCGTATACCCACCTTTAGC |
| 43 | S |  | GGCATCCTCAATAGTAGAAGCCGGGGCGGGCACTGGATGAACCGTATACCCACCTTTAGC |
| 44 | S |  | GGCATCCTCAATAGTAGAAGCCGGGGCGGGTACTGGATGAACCGAATACCCACCCTTAGC |

APPENDIX-continued

Key-Species codes:
*Bos tarrus*-B
*Sus scrofa*-S
*Ovis Aries*-O
*Equus caballus*-E
*Canis lupus*-C
*Mus musculus*-M
*Felis catus*-F

| SEQ ID NO. | Species code | Designation | Sequence |
|---|---|---|---|
| 45 | S | | GGCATCCTCAATAGTAAAAGCCGGGGCGGGTACTGGATGAACCGTATACCCACCTTTAGC |
| 46 | S | | GGCATCCTCAATAGTAGAAGCCGGGGCGGGTACCGGATGAACCGTATACCCACCTTTAGC |
| 47 | S | | GGCATCCTCAATAGTAGAAGCCGGAGCGGGTACTGGATGAACCGTATACCCACCTTTAGC |
| 48 | S | | GGCATCCTCAATAGTAGAAGCCGGGGCGGGTACTGGATGAGCCGTATACCCACCTTTAGC |
| 49 | S | | GGCATCCTCAATAGTAGAAGCCGGAGCGGGTACTGGATGAACTGTATATCCACCTTTAGC |
| 50 | S | | GGCATCCTCAATAGTAGAGGCCGGAGCGGGTACTGGATGAACTGTATACCCGCCTTTAGC |
| 51 | S | | GGCATCCTCAATAGTAGAGGCCGGAGCGGGTACTGGATGAACTGTATACCCACCTTTAGC |
| 52 | S | | GGCGTCCTCAATAGTAGAAGCCGGAGCGGGTACTGGATGAACTGTATACCCACCTTTAGC |
| 53 | S | P5a | CAATAGTAGAAGCCGGAGCGGGTACTGGATGAACTGTATACCCACCTTTAGCTGGAAACTTAGCCCATGC |
| 54 | S | P5b | CAATAGTAGAAGCCGGGGCGGGTACTGGATGAACCGTATACCCACCTTTAGCTGGAAACTTAGCCCATGC |
| 55 | S | | CAATAGTAGAAGCCGGAGCGGGTACTGGATGAACCGTATACCCACCTTTAGCTGGAAACTTAGCCCATGC |
| 56 | S | | CAATAGTAGAGGCCGGAGCGGGTACTGGATGAACTGTATACCCACCTTTAGCTGGAAACTTAGCCCACGC |
| 57 | S | | CAATAGTAGAGGCCGGAGCGGGTACTGGATGAACTGTATACCCGCCTTTAGCTGGAAACTTAGCCCACGC |
| 58 | S | | CAATAGTAGAAGCCGGGGCGGGTACTGGATGAGCCGTATACCCACCTTTAGCTGGAAACTTAGCCCATGC |
| 59 | S | | CAATAGTAGAAGCCGGGGCGGGCACTGGATGAACCGTATACCCACCTTTAGCTGGAAACTTAGCCCATGC |
| 60 | S | | CAATAGTAGAAGCCGGGGCGGGTACTGGATGAACCGTATACCCACCTTTAGCTGGAAACTTACCCCATGC |
| 61 | S | | CAATAGTAGAAGCCGGGGCGGGTACTGGATGAACCGAATACCCACCCTTAGCTGGAAACTTAGCCCAAGC |
| 62 | S | | CAATAGTAGAAGCCGGGGCGGGTACTGGATGAACCGTATACCCACCTTTAGCTGGAAACTTAGCCCGTGC |
| 63 | S | | CAATAGTAGAAGCCGGGGCGGGTACTGGATGAACCGTATACCCACCTTTAGCCGGAAACTTAGCCCATGC |
| 64 | S | | CAATAGTAGAAGCCGGGGCGGGTACCGGATGAACCGTATACCCACCTTTAGCTGGAAACTTAGCCCATGC |
| 65 | S | | CAATAGTAAAAGCCGGGGCGGGTACTGGATGAACCGTATACCCACCTTTAGCTGGAAACTTAGCCCATGC |
| 66 | S | | CAATAGTAGAAGCCGGAGCGGGTACTGGATGAACTGTATATCCACCTTTAGCTGGAAACTTGGCCCATGC |

APPENDIX-continued

Key-Species codes:
*Bos tarrus*-B
*Sus scrofa*-S
*Ovis Aries*-O
*Equus caballus*-E
*Canis lupus*-C
*Mus musculus*-M
*Felis catus*-F

| SEQ ID NO. | Species code | Designation | Sequence |
|---|---|---|---|
| 67 | S | P6a | ATAGTAGAAGCCGGAGCGGGTACTGGATGAACTGTATACCCACCTTTAGCTGGAAACTTAGCCCATGCAG |
| 68 | S | P6b | ATAGTAGAAGCCGGGGCGGGTACTGGATGAACCGTATACCCACCTTTAGCTGGAAACTTAGCCCATGCAG |
| 69 | S |  | ATAGTAGAGGCCGGAGCGGGTACTGGATGAACTGTATACCCACCTTTAGCTGGAAACTTAGCCCACGCAG |
| 70 | S |  | ATAGTAGAGGCCGGAGCGGGTACTGGATGAACTGTATACCCGCCTTTAGCTGGAAACTTAGCCCACGCAG |
| 71 | S |  | ATAGTAGAAGCCGGGGCGGGTACTGGATGAGCCGTATACCCACCTTTAGCTGGAAACTTAGCCCATGCAG |
| 72 | S |  | ATAGTAGAAGCCGGGGCGGGCACTGGATGAACCGTATACCCACCTTTAGCTGGAAACTTAGCCCATGCAG |
| 73 | S |  | ATAGTAGAAGCCGGGGCGGGTACTGGATGAACCGTATACCCACCTTTAGCTGGAAACTTACCCCATGCAG |
| 74 | S |  | ATAGTAGAAGCCGGGGCGGGTACTGGATGAACCGAATACCCACCCTTAGCTGGAAACTTAGCCCAAGCAG |
| 75 | S |  | ATAGTAGAAGCCGGGGCGGGTACTGGATGAACCGTATACCCACCTTTAGCTGGAAACTTAGCCCGTGCAG |
| 76 | S |  | ATAGTAGAAGCCGGGGCGGGTACTGGATGAACCGTATACCCACCTTTAGCCGGAAACTTAGCCCATGCAG |
| 77 | S |  | ATAGTAGAAGCCGGGGCGGGTACCGGATGAACCGTATACCCACCTTTAGCTGGAAACTTAGCCCATGCAG |
| 78 | S |  | ATAGTAAAAGCCGGGGCGGGTACTGGATGAACCGTATACCCACCTTTAGCTGGAAACTTAGCCCATGCAG |
| 79 | S |  | ATAGTAGAAGCCGGAGCGGGTACTGGATGAACTGTATATCCACCTTTAGCTGGAAACTTGGCCCATGCAG |
| 80 | O | P7a | GCCCATGCAGGAGCCTCAGTAGATCTAACTATTTTCTCCCTACATCTGGCAGGTGTCTCT |
| 81 | O | P7b | GCCCATGCAGGAGCCTCAGTAGACCTAACTATTTTCTCCCTACACCTGGCAGGTGTCTCT |
| 82 | O | P7c | GCCCATGCAGGAGCCTCAGTAGATCTAATTATTTTCTCCCTACACCTGGCAGGTGTCTCT |
| 83 | O | P7d | GCCCATGCAGGAGCCTCAGTAGATCTAACTATTTTCTCCCTACACCTGGCAGGTGTCTCT |
| 84 | O | P5a | AGCCCATGCAGGAGCCTCAGTAGATCTAACTATTTTCTCCCTACATCTGGCAGGTGTCTC |
| 85 | O | P5b | AGCCCATGCAGGAGCCTCAGTAGACCTAACTATTTTCTCCCTACACCTGGCAGGTGTCTC |
| 86 | O | P5c | AGCCCATGCAGGAGCCTCAGTAGATCTAATTATTTTCTCCCTACACCTGGCAGGTGTCTC |
| 87 | O | P5d | AGCCCATGCAGGAGCCTCAGTAGATCTAACTATTTTCTCCCTACACCTGGCAGGTGTCTC |
| 88 | O | P4a | CTAGCCCATGCAGGAGCCTCAGTAGATCTAACTATTTTCTCCCTACATCTGGCAGGTGTC |

APPENDIX-continued

Key-Species codes:
*Bos tarrus*-B
*Sus scrofa*-S
*Ovis Aries*-O
*Equus caballus*-E
*Canis lupus*-C
*Mus musculus*-M
*Felis catus*-F

| SEQ ID NO. | Species code | Designation | Sequence |
|---|---|---|---|
| 89 | O | P4b | CTAGCCCATGCAGGAGCCTCAGTAGACCTAACTATTTTCTCCCTACACCTGGCAGGTGTC |
| 90 | O | P4c | CTAGCCCATGCAGGAGCCTCAGTAGATCTAATTATTTTCTCCCTACACCTGGCAGGTGTC |
| 91 | O | P4d | CTAGCCCATGCAGGAGCCTCAGTAGATCTAACTATTTTCTCCCTACACCTGGCAGGTGTC |
| 92 | O | P6a | CCTAGCCCATGCAGGAGCCTCAGTAGATCTAACTATTTTCTCCCTACATCTGGCAGGTGT |
| 93 | O | P6b | CCTAGCCCATGCAGGAGCCTCAGTAGACCTAACTATTTTCTCCCTACACCTGGCAGGTGT |
| 94 | O | P6c | CCTAGCCCATGCAGGAGCCTCAGTAGATCTAATTATTTTCTCCCTACACCTGGCAGGTGT |
| 95 | O | P6d | CCTAGCCCATGCAGGAGCCTCAGTAGATCTAACTATTTTCTCCCTACACCTGGCAGGTGT |
| 96 | O | P2 | GCAACCTAGCCCATGCAGGAGCCTCAGTAGATCTAACTATTTTCTCCCTACATCTGGCAGGTGTCTCTTC |
| 97 | O |  | GCAACCTAGCCCATGCAGGAGCCTCAGTAGATCTAACTATTTTCTCCCTACACCTGGCAGGTGTCTCTTC |
| 98 | O |  | GCAACCTAGCCCATGCAGGAGCCTCAGTAGATCTAATTATTTTCTCCCTACACCTGGCAGGTGTCTCTTC |
| 99 | O |  | GCAACCTAGCCCATGCAGGAGCCTCAGTAGACCTAACTATTTTCTCCCTACACCTGGCAGGTGTCTCTTC |
| 100 | O | P3 | GGCAACCTAGCCCATGCAGGAGCCTCAGTAGATCTAACTATTTTCTCCCTACATCTGGCAGGTGTCTCTT |
| 101 | O |  | GGCAACCTAGCCCATGCAGGAGCCTCAGTAGATCTAACTATTTTCTCCCTACACCTGGCAGGTGTCTCTT |
| 102 | O |  | GGCAACCTAGCCCATGCAGGAGCCTCAGTAGATCTAATTATTTTCTCCCTACACCTGGCAGGTGTCTCTT |
| 103 | O |  | GGCAACCTAGCCCATGCAGGAGCCTCAGTAGACCTAACTATTTTCTCCCTACACCTGGCAGGTGTCTCTT |
| 104 | E | P1 | TGAACCGTATATCCTCCTCTAGCTGGAAATCTGGCGCATGCAGGAGCCTCTGTTGACTTA |
| 105 | E | P2 | GAACCGTATATCCTCCTCTAGCTGGAAATCTGGCGCATGCAGGAGCCTCTGTTGACTTAA |
| 106 | E | P3 | CTGAACCGTATATCCTCCTCTAGCTGGAAATCTGGCGCATGCAGGAGCCTCTGTTGACTT |
| 107 | E | P4 | AACCGTATATCCTCCTCTAGCTGGAAATCTGGCGCATGCAGGAGCCTCTGTTGACTTAAC |
| 108 | E | P5 | CCTCTAGCTGGAAATCTGGCGCATGCAGGAGCCTCTGTTGACTTAACCATTTTCTCTCTC |
| 109 | E | P6 | CTCTAGCTGGAAATCTGGCGCATGCAGGAGCCTCTGTTGACTTAACCATTTTCTCTCTCC |
| 110 | E | P7 | CTAGCTGGAAATCTGGCGCATGCAGGAGCCTCTGTTGACTTAACCATTTTCTCTCTCCAC |

APPENDIX-continued

Key-Species codes:
*Bos tarrus*-B
*Sus scrofa*-S
*Ovis Aries*-O
*Equus caballus*-E
*Canis lupus*-C
*Mus musculus*-M
*Felis catus*-F

| SEQ ID NO. | Species code | Designation | Sequence |
|---|---|---|---|
| 111 | E | P8a | GCTGGAAATCTGGCGCATGCAGGAGCCTCTGTTGACTTAACCATTTTCTCTCTCCACCTA |
| 112 | E | P8b | GCTGGAAATCTGGCGCATGCAGGAGCCTCTGTTGACTTAACCATTTTCTCTCTCCACCTG |
| 113 | E | P9a | CTGGAAATCTGGCGCATGCAGGAGCCTCTGTTGACTTAACCATTTTCTCTCTCCACCTAG |
| 114 | E | P9b | CTGGAAATCTGGCGCATGCAGGAGCCTCTGTTGACTTAACCATTTTCTCTCTCCACCTCG |
| 115 | E | P10a | TGGAAATCTGGCGCATGCAGGAGCCTCTGTTGACTTAACCATTTTCTCTCTCCACCTAGC |
| 116 | E | P10b | TGGAAATCTGGCGCATGCAGGAGCCTCTGTTGACTTAACCATTTTCTCTCTCCACCTGGC |
| 117 | E | P11a | GGAAATCTGGCGCATGCAGGAGCCTCTGTTGACTTAACCATTTTCTCTCTCCACCTAGCT |
| 118 | E | P11b | GGAAATCTGGCGCATGCAGGAGCCTCTGTTGACTTAACCATTTTCTCTCTCCACCTGGCT |
| 119 | E | P12a | GAAATCTGGCGCATGCAGGAGCCTCTGTTGACTTAACCATTTTCTCTCTCCACCTAGCTG |
| 120 | E | P12b | GAAATCTGGCGCATGCAGGAGCCTCTGTTGACTTAACCATTTTCTCTCTCCACCTGGCTG |
| 121 | E | P13 | TCCTCCTCTAGCTGGAAATCTGGCGCATGCAGGAGCCTCTGTTGACTTAACCATTTTCTC |
| 122 | E | P14 | CCTCCTCTAGCTGGAAATCTGGCGCATGCAGGAGCCTCTGTTGACTTAACCATTTTCTCT |
| 123 | E | P15 | CTCCTCTAGCTGGAAATCTGGCGCATGCAGGAGCCTCTGTTGACTTAACCATTTTCTCTC |
| 124 | E | P16 | CGTATATCCTCCTCTAGCTGGAAATCTGGCGCATGCAGGAGCCTCTGTTGACTTAACCAT |
| 125 | E | P17 | ACCGTATATCCTCCTCTAGCTGGAAATCTGGCGCATGCAGGAGCCTCTGTTGACTTAACC |
| 126 | E | P18 | CCGTATATCCTCCTCTAGCTGGAAATCTGGCGCATGCAGGAGCCTCTGTTGACTTAACCA |
| 127 | E | P12 | TATCCTCCTCTAGCTGGAAATCTGGCGCATGCAGGAGCCTCTGTTGACTTAACCATTTTCTCTCTCCACC |
| 128 | E | P13 | ATCCTCCTCTAGCTGGAAATCTGGCGCATGCAGGAGCCTCTGTTGACTTAACCATTTTCTCTCTCCACCT |
| 129 | E | P14 | GGCTGAACCGTATATCCTCCTCTAGCTGGAAATCTGGCGCATGCAGGAGCCTCTGTTGACTTAACCATTT |
| 130 | E | P15 | AGGCTGAACCGTATATCCTCCTCTAGCTGGAAATCTGGCGCATGCAGGAGCCTCTGTTGACTTAACCATT |
| 131 | E | P6a | CCTCTAGCTGGAAATCTGGCGCATGCAGGAGCCTCTGTTGACTTAACCATTTTCTCTCTCCACCTAGCTG |

APPENDIX-continued

Key-Species codes:
*Bos tarrus*-B
*Sus scrofa*-S
*Ovis Aries*-O
*Equus caballus*-E
*Canis lupus*-C
*Mus musculus*-M
*Felis catus*-F

| SEQ ID NO. | Species code | Designation | Sequence |
|---|---|---|---|
| 132 | E | P6b | CCTCTAGCTGGAAATCTGGCGCATGCAGGAGCCTCTGTTGACTTAACCATTTTCT CTCTCCACCTGGCTG |
| 133 | E | P7a | TCCTCCTCTAGCTGGAAATCTGGCGCATGCAGGAGCCTCTGTTGACTTAACCATT TTCTCTCTCCACCTA |
| 134 | E | P7b | TCCTCCTCTAGCTGGAAATCTGGCGCATGCAGGAGCCTCTGTTGACTTAACCATT TTCTCTCTCCACCTG |
| 135 | E | P8a | TCCTCTAGCTGGAAATCTGGCGCATGCAGGAGCCTCTGTTGACTTAACCATTTTC TCTCTCCACCTAGCT |
| 136 | E | P8b | TCCTCTAGCTGGAAATCTGGCGCATGCAGGAGCCTCTGTTGACTTAACCATTTTC TCTCTCCACCTGGCT |
| 137 | E | P9a | CCTCCTCTAGCTGGAAATCTGGCGCATGCAGGAGCCTCTGTTGACTTAACCATTT TCTCTCTCCACCTAG |
| 138 | E | P9b | CCTCCTCTAGCTGGAAATCTGGCGCATGCAGGAGCCTCTGTTGACTTAACCATTT TCTCTCTCCACCTGG |
| 139 | E | P10a | CTCCTCTAGCTGGAAATCTGGCGCATGCAGGAGCCTCTGTTGACTTAACCATTTT CTCTCTCCACCTAGC |
| 140 | E | P10b | CTCCTCTAGCTGGAAATCTGGCGCATGCAGGAGCCTCTGTTGACTTAACCATTTT CTCTCTCCACCTGGC |
| 141 | C | P1a | CCTCCTCATCCGAGCCGAACTAGGTCAGCCCGGTACTTTACTAGGTGACGATCA AATTTA |
| 142 | C | P1b | CCTCCTCATCCGAGCCGAACTAGGTCAGCCCGGTACTTTACTAGGTGATGATCA AATTTA |
| 143 | C | P1c | CCTCCTCATCCGAGCCGAACTAGGTCAGCCCGGTACTTTACTAGGCGACGATCA AATTTA |
| 144 | C | | CCTCCTCATCCGGGCCGAACTAGGTCAGCCCGGTACTTTACTAGGTGACGATCA AATTTA |
| 145 | C | | CCTCCTCATCCGAGCCGAACTAGGTCAGCCCGGTACTTTACTAGGAGACGATCA GATTTA |
| 146 | C | P2 | AGCCTCCTCATCCGAGCCGAACTAGGTCAGCCCGGTACTTTACTAGGTGACGAT CAAATT |
| 147 | C | | AGCCTCCTCATCCGAGCCGAACTAGGTCAGCCCGGTACTTTACTAGGTGATGAT CAAATT |
| 148 | C | | AGCCTCCTCATCCGAGCCGAACTAGGTCAGCCCGGTACTTTACTAGGCGACGAT CAAATT |
| 149 | C | | AGCCTCCTCATCCGGGCCGAACTAGGTCAGCCCGGTACTTTACTAGGTGACGAT CAAATT |
| 150 | C | | AGCCTCCTCATCCGAGCCGAACTAGGTCAGCCCGGTACTTTACTAGGAGACGAT CAGATT |
| 151 | C | P3 | GCCTCCTCATCCGAGCCGAACTAGGTCAGCCCGGTACTTTACTAGGTGACGATC AAATTT |
| 152 | C | | GCCTCCTCATCCGAGCCGAACTAGGTCAGCCCGGTACTTTACTAGGTGATGATC AAATTT |
| 153 | C | | GCCTCCTCATCCGAGCCGAACTAGGTCAGCCCGGTACTTTACTAGGCGACGATC AAATTT |

APPENDIX-continued

Key-Species codes:
*Bos tarrus*-B
*Sus scrofa*-S
*Ovis Aries*-O
*Equus caballus*-E
*Canis lupus*-C
*Mus musculus*-M
*Felis catus*-F

| SEQ ID NO. | Species code | Designation | Sequence |
|---|---|---|---|
| 154 | C |  | GCCTCCTCATCCGGGCCGAACTAGGTCAGCCCGGTACTTTACTAGGTGACGATCAAATTT |
| 155 | C | P4a | CACTGCTTTGAGCCTCCTCATCCGAGCCGAACTAGGTCAGCCCGGTACTTTACTAGGTGACGATCAAATT |
| 156 | C | P4b | CACTGCCTTGAGCCTCCTCATCCGAGCCGAACTAGGTCAGCCCGGTACTTTACTAGGTGACGATCAAATT |
| 157 | C |  | CACTGCCTTGAGCCTCCTCATCCGAGCCGAACTAGGTCAGCCCGGTACTTTACTAGGTGATGATCAAATT |
| 158 | C |  | CACTGCCTTGAGCCTCCTCATCCGAGCCGAACTAGGTCAGCCCGGTACTTTACTAGGCGACGATCAAATT |
| 159 | C |  | CACTGCCTTGAGCCTCCTCATCCGAGCCGAGCTAGGTCAGCCCGGTACTTTACTAGGCGACGACCAAATT |
| 160 | C | P3a | CTGCTTTGAGCCTCCTCATCCGAGCCGAACTAGGTCAGCCCGGTACTTTACTAGGTGACGATCAAATTTA |
| 161 | C | P3b | CTGCCTTGAGCCTCCTCATCCGAGCCGAACTAGGTCAGCCCGGTACTTTACTAGGTGACGATCAAATTTA |
| 162 | C |  | CTGCCTTGAGCCTCCTCATCCGAGCCGAACTAGGTCAGCCCGGTACTTTACTAGGTGATGATCAAATTTA |
| 163 | C |  | CTGCCTTGAGCCTCCTCATCCGAGCCGAACTAGGTCAGCCCGGTACTTTACTAGGCGACGATCAAATTTA |
| 164 | C |  | CTGCCTTGAGCCTCCTCATCCGAGCCGAGCTAGGTCAGCCCGGTACTTTACTAGGCGACGACCAAATTTA |
| 165 | C | P2a | ACTGCTTTGAGCCTCCTCATCCGAGCCGAACTAGGTCAGCCCGGTACTTTACTAGGTGACGATCAAATTT |
| 166 | C | P2b | ACTGCCTTGAGCCTCCTCATCCGAGCCGAACTAGGTCAGCCCGGTACTTTACTAGGTGACGATCAAATTT |
| 167 | C |  | ACTGCCTTGAGCCTCCTCATCCGAGCCGAACTAGGTCAGCCCGGTACTTTACTAGGTGATGATCAAATTT |
| 168 | C |  | ACTGCCTTGAGCCTCCTCATCCGAGCCGAACTAGGTCAGCCCGGTACTTTACTAGGCGACGATCAAATTT |
| 169 | C |  | ACTGCCTTGAGCCTCCTCATCCGAGCCGAGCTAGGTCAGCCCGGTACTTTACTAGGCGACGACCAAATTT |
| 170 | M | P3 | CAATAGTAGAAGCAGGAGCAGGAACAGGATGAACAGTCTACCCACCTCTAGCCGGAAATC |
| 171 | M | P4 | TAGTAGAAGCAGGAGCAGGAACAGGATGAACAGTCTACCCACCTCTAGCCGGAAATCTAG |
| 172 | M |  | TAGTAGAAGCAGGAGCAGGAACAGGATGAACAGTCTACCCACCTCTAGCCGGAAATCCAG |
| 173 | M | P5 | AGTAGAAGCAGGAGCAGGAACAGGATGAACAGTCTACCCACCTCTAGCCGGAAATCTAGC |
| 174 | M |  | AGTAGAAGCAGGAGCAGGAACAGGATGAACAGTCTACCCACCTCTAGCCGGAAATCCAGT |
| 175 | M | P6 | GTCTACCCACCTCTAGCCGGAAATCTAGCCCATGCAGGAGCATCAGTAGACCTAACAATT |

APPENDIX-continued

Key-Species codes:
*Bos tarrus*-B
*Sus scrofa*-S
*Ovis Aries*-O
*Equus caballus*-E
*Canis lupus*-C
*Mus musculus*-M
*Felis catus*-F

| SEQ ID NO. | Species code | Designation | Sequence |
|---|---|---|---|
| 176 | M | | GTCTACCCACCTCTAGCCGGAAATCCAGTCCATGCAGGAGCATCAGTAGACCTAACAATT |
| 177 | M | | GTCTACCCACCTCTAGCCGGAAATCTAGCCCATGCAGGAGCATCAGTAGATCTAACAATT |
| 178 | M | P7 | CCCACCTCTAGCCGGAAATCTAGCCCATGCAGGAGCATCAGTAGACCTAACAATTTTCTC |
| 179 | M | | CCCACCTCTAGCCGGAAATCCAGTCCATGCAGGAGCATCAGTAGACCTAACAATTTTCTC |
| 180 | M | | CCCACCTCTAGCCGGAAATCTAGCCCATGCAGGAGCATCAGTAGATCTAACAATTTTCTC |
| 181 | M | P8 | CCACCTCTAGCCGGAAATCTAGCCCATGCAGGAGCATCAGTAGACCTAACAATTTTCTCC |
| 182 | M | | CCACCTCTAGCCGGAAATCCAGTCCATGCAGGAGCATCAGTAGACCTAACAATTTTCTCC |
| 183 | M | | CCACCTCTAGCCGGAAATCTAGCCCATGCAGGAGCATCAGTAGATCTAACAATTTTCTCC |
| 184 | M | P9 | AGGATGAACAGTCTACCCACCTCTAGCCGGAAATCTAGCCCATGCAGGAGCATCAGTAGA |
| 185 | M | | AGGATGAACAGTCTACCCACCTCTAGCCGGAAATCCAGTCCATGCAGGAGCATCAGTAGA |
| 186 | M | | AGGATGAACCGTATATCCACCTTTAGCCGGAAATITAGCCCACGCCGGAGCATCAGTGA |
| 187 | M | P10 | AGTCTACCCACCTCTAGCCGGAAATCTAGCCCATGCAGGAGCATCAGTAGACCTAACAAT |
| 188 | M | | AGTCTACCCACCTCTAGCCGGAAATCCAGTCCATGCAGGAGCATCAGTAGACCTAACAAT |
| 189 | M | | AGTCTACCCACCTCTAGCCGGAAATCTAGCCCATGCAGGAGCATCAGTAGATCTAACAAT |
| 190 | M | P11 | ATGAACAGTCTACCCACCTCTAGCCGGAAATCTAGCCCATGCAGGAGCATCAGTAGACCT |
| 191 | M | | ATGAACAGTCTACCCACCTCTAGCCGGAAATCCAGTCCATGCAGGAGCATCAGTAGACCT |
| 192 | M | | ATGAACAGTCTACCCACCTCTAGCCGGAAATCTAGCCCATGCAGGAGCATCAGTAGATCT |
| 193 | M | P12 | TGAACAGTCTACCCACCTCTAGCCGGAAATCTAGCCCATGCAGGAGCATCAGTAGACCTA |
| 194 | M | | TGAACAGTCTACCCACCTCTAGCCGGAAATCCAGTCCATGCAGGAGCATCAGTAGACCTA |
| 195 | M | | TGAACAGTCTACCCACCTCTAGCCGGAAATCTAGCCCATGCAGGAGCATCAGTAGATCTA |
| 196 | M | P13 | GAACAGTCTACCCACCTCTAGCCGGAAATCTAGCCCATGCAGGAGCATCAGTAGACCTAA |
| 197 | M | | GAACAGTCTACCCACCTCTAGCCGGAAATCCAGTCCATGCAGGAGCATCAGTAGACCTAA |

APPENDIX-continued

Key-Species codes:
*Bos tarrus*-B
*Sus scrofa*-S
*Ovis Aries*-O
*Equus caballus*-E
*Canis lupus*-C
*Mus musculus*-M
*Felis catus*-F

| SEQ ID NO. | Species code | Designation | Sequence |
|---|---|---|---|
| 198 | M | | GAACAGTCTACCCACCTCTAGCCGGAAATCTAGCCCATGCAGGAGCATCAGTAGATCTAA |
| 199 | M | P14 | AACAGTCTACCCACCTCTAGCCGGAAATCTAGCCCATGCAGGAGCATCAGTAGACCTAAC |
| 200 | M | | AACAGTCTACCCACCTCTAGCCGGAAATCCAGTCCATGCAGGAGCATCAGTAGACCTAAC |
| 201 | M | | AACAGTCTACCCACCTCTAGCCGGAAATCTAGCCCATGCAGGAGCATCAGTAGATCTAAC |
| 202 | M | P15 | ACAGTCTACCCACCTCTAGCCGGAAATCTAGCCCATGCAGGAGCATCAGTAGACCTAACA |
| 203 | M | | ACAGTCTACCCACCTCTAGCCGGAAATCCAGTCCATGCAGGAGCATCAGTAGACCTAACA |
| 204 | M | | ACAGTCTACCCACCTCTAGCCGGAAATCTAGCCCATGCAGGAGCATCAGTAGATCTAACA |
| 205 | M | P16 | CAGTCTACCCACCTCTAGCCGGAAATCTAGCCCATGCAGGAGCATCAGTAGACCTAACAA |
| 206 | M | | CAGTCTACCCACCTCTAGCCGGAAATCCAGTCCATGCAGGAGCATCAGTAGACCTAACAA |
| 207 | M | | CAGTCTACCCACCTCTAGCCGGAAATCTAGCCCATGCAGGAGCATCAGTAGATCTAACAA |
| 208 | M | P1 | TCAATAGTAGAAGCAGGAGCAGGAACAGGATGAACAGTCTACCCACCTCTAGCCGGAAATCTAGCCCATG |
| 209 | M | | TCAATAGTAGAAGCAGGAGCAGGAACAGGATGAACAGTCTACCCACCTCTAGCCGGAAATCCAGTCCATG |
| 210 | M | P2 | CAATAGTAGAAGCAGGAGCAGGAACAGGATGAACAGTCTACCCACCTCTAGCCGGAAATCTAGCCCATGC |
| 211 | M | | CAATAGTAGAAGCAGGAGCAGGAACAGGATGAACAGTCTACCCACCTCTAGCCGGAAATCCAGTCCATGC |
| 212 | M | P3 | GTCTACCCACCTCTAGCCGGAAATCTAGCCCATGCAGGAGCATCAGTAGACCTAACAATTTTCTCCCTTC |
| 213 | M | | GTCTACCCACCTCTAGCCGGAAATCTAGCCCATGCAGGAGCATCAGTAGACCTAACAATTTTCTCCCTCC |
| 214 | M | | GTCTACCCACCTCTAGCCGGAAATCTAGCCCATGCAGGAGCATCAGTAGATCTAACAATTTTCTCCCTTC |
| 215 | M | | GTCTACCCACCTCTAGCCGGAAATCCAGTCCATGCAGGAGCATCAGTAGACCTAACAATTTTCTCCCTTC |
| 216 | M | P4 | CAGGATGAACAGTCTACCCACCTCTAGCCGGAAATCTAGCCCATGCAGGAGCATCAGTAGACCTAACAAT |
| 217 | M | | CAGGATGAACAGTCTACCCACCTCTAGCCGGAAATCTAGCCCATGCAGGAGCATCAGTAGATCTAACAAT |
| 218 | M | | CAGGATGAACAGTCTACCCACCTCTAGCCGGAAATCCAGTCCATGCAGGAGCATCAGTAGACCTAACAAT |
| 219 | F | P1 | GAGCTTCTGACTCCTCCCTCCATCCTTTCTACTCTTACTCGCCTCATCTATGGTAGAAGC |

APPENDIX-continued

Key-Species codes:
*Bos tarrus*-B
*Sus scrofa*-S
*Ovis Aries*-O
*Equus caballus*-E
*Canis lupus*-C
*Mus musculus*-M
*Felis catus*-F

| SEQ ID NO. | Species code | Designation | Sequence |
|---|---|---|---|
| 220 | F |  | GAGCTTCTGACTCCTCCCCCCATCCTTTCTACTCTTACTCGCCTCATCTATGGTAGAAGC |
| 221 | F | P2a | GAGCTTCTGACTCCTCCCTCCATCCTTTCTACTCCTACTCGCCTCATCTATGGTAGAAGC |
| 222 | F | P2b | CTCCCTCCATCCTTTCTACTCTTACTCGCCTCATCTATGGTAGAAGCCGGAGCAGGAACT |
| 223 | F | P2c | CTCCCCCCATCCTTTCTACTCTTACTCGCCTCATCTATGGTAGAAGCCGGAGCAGGAACT |
| 224 | F | P3 | CTCCCTCCATCCTTTCTACTCCTACTCGCCTCATCTATGGTAGAAGCCGGAGCAGGAACT |
| 225 | F |  | TCCTCCCTCCATCCTTTCTACTCTTACTCGCCTCATCTATGGTAGAAGCCGGAGCAGGAA |
| 226 | F |  | TCCTCCCCCATCCTTTCTACTCTTACTCGCCTCATCTATGGTAGAAGCCGGAGCAGGAA |
| 227 | F |  | TCCTCCCTCCATCCTTTCTACTCCTACTCGCCTCATCTATGGTAGAAGCCGGAGCAGGAA |
| 228 | F | P4 | TGACTCCTCCCTCCATCCTTTCTACTCTTACTCGCCTCATCTATGGTAGAAGCCGGAGCA |
| 229 | F |  | TGACTCCTCCCCCCATCCTTTCTACTCTTACTCGCCTCATCTATGGTAGAAGCCGGAGCA |
| 230 | F |  | TGACTCCTCCCTCCATCCTTTCTACTCCTACTCGCCTCATCTATGGTAGAAGCCGGAGCA |
| 231 | F | P6 | GCTCCTGACATAGCATTTCCCCGAATAAACAACATGAGCTTCTGACTCCTCCCTCCATCC |
| 232 | F |  | GCTCCTGACATAGCATTTCCCCGAATAAACAACATGAGCTTCTGACTCCTCCCCCCATCC |
| 233 | F | P1 | ATGAGCTTCTGACTCCTCCCTCCATCCTTTCTACTCTTACTCGCCTCATCTATGGTAGAAGCCGGAGCAG |
| 234 | F |  | ATGAGCTTCTGACTCCCCCCCCCATCCTTTCTACTCTTACTCGCCTCATCTATGGTAGAAGCCGGAGCAG |
| 235 | F |  | ATGAGCTTCTGACTCCTCCCTCCATCCTTTCTACTCCTACTCGCCTCATCTATGGTAGAAGCCGGAGCAG |
| 236 | F | P2 | AGCTTCTGACTCCTCCCTCCATCCTTTCTACTCTTACTCGCCTCATCTATGGTAGAAGCCGGAGCAGGAA |
| 237 | F |  | AGCTTCTGACTCCCCCCCCCATCCTTTCTACTCTTACTCGCCTCATCTATGGTAGAAGCCGGAGCAGGAA |
| 238 | F |  | AGCTTCTGACTCCTCCCTCCATCCTTTCTACTCCTACTCGCCTCATCTATGGTAGAAGCCGGAGCAGGAA |
| 239 | F | P3 | CTTCTGACTCCTCCCTCCATCCTTTCTACTCTTACTCGCCTCATCTATGGTAGAAGCCGGAGCAGGAACT |
| 240 | F |  | CTTCTGACTCCCCCCCCCATCCTTTCTACTCTTACTCGCCTCATCTATGGTAGAAGCCGGAGCAGGAACT |
| 241 | F |  | CTTCTGACTCCTCCCTCCATCCTTTCTACTCCTACTCGCCTCATCTATGGTAGAAGCCGGAGCAGGAACT |

The invention claimed is:

1. A method of rapid identification of a mammalian species origin or mammalian species origins of a sample, comprising sequential steps of:
   a) engineering DNA probes with a length from 60 to 80 bases; said engineering including identifying regions from $48^{th}$ to $705^{th}$ bp of double stranded COI gene region of a first mammalian species for yielding a first group of 60-80 bp DNA regions of interest, and from the first group of 60-80 bp of DNA regions of the double stranded COI gene region, identifying a second group of 60-80 bp DNA regions of single-stranded sequences of the double stranded COI gene region meeting a combination of the following criteria:
      i) with a GC content 50 to 52%;
      ii) with a positive value of delta G at a given temperature, wherein the given temperature is a hybridization temperature ($T_{hyb}$) of 15-25° C. below a melting temperature ($T_m$), wherein the hybridization temperature ($T_{hyb}$) is a temperature at which the DNA probes hybridize during identification, and wherein the melting temperature ($T_m$) is a temperature at which the double stranded sequence at a region corresponding to the second group of 60-80 bp DNA regions dissociates; and
      iii) in which difference between the number of secondary structures (SS) of any of the DNA regions in the second group of 60-80 bp DNA regions and the value of secondary structure (SS) of the respective DNA region is between 0 to 4, thus yielding a third group of DNA regions, wherein the value of the secondary structure is determined based on propensity of a base of single-stranded DNA molecules;
   b) producing the DNA probes corresponding to sequences of the third group of DNA regions, wherein the sequences of the DNA probes are comprised in the group consisting of SEQ ID NOs. 1-241;
   c) collecting the sample;
   d) dividing the sample into a number of portions for situation in a multi-well container or containers;
   e) providing the produced DNA probes from step b), wherein the number of the sample portions is greater than the number of mammalian species types from which the DNA probes derive;
   f) selecting some or all of the DNA probes, and allocating the selected DNA probes in the multi-well container or the containers, such that each of the selected DNA probes is situated separately, for hybridization with the sample portions, respectively;
   g) contacting the sample portions for intended hybridization with the selected DNA probes simultaneously;
   h) analyzing the sample portions contained in the multi-well container or containers for a positive hybridization results following the contacting step; and
   i) determining the mammalian species origin or origins of the sample according to positive hybridization results.

2. A method as claimed in claim 1, allowing the hybridization to occur in a medium with a salt concentration of 50 mmole.

3. A method as claimed in claim 2, wherein the salt is sodium chloride.

4. method as claimed in claim 3, wherein the medium is free of organic solvent.

5. A method as claimed in claim 1, wherein the species include *Bos Taurus* (cattle), *Sus scrofa* (pig), *Ovis aries* (sheep), *Equus caballus* (horse), *Canis lupus* (dog) and *Mus musculus* (mouse) and *Felis Catus* (cat).

* * * * *

SEQUENCE LISTING

<160> NUMBER OF SEQ ID NOS: 241

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
tccgtaataa ttaccgccgt actactacta ctctcgctcc ctgtattagc agccggcatc        60

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
ccgtaataat taccgccgta ctactactac tctcgctccc tgtattagca gccggcatca        60

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
cgtaataatt accgccgtac tactactact ctcgctccct gtattagcag ccggcatcac        60

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
ccggaaccta aatacaacct tcttcgaccc ggcaggagga ggagacccta ttctatatca        60

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
ccgaaaccta aatacaacct tcttcgaccc ggcaggagga ggagacccta ttctatatca        60

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
ccggaaccta aatacaactt tcttcgaccc ggcaggagga ggagatccta ttctatacca        60

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
agcctactaa ttcgcgctga actaggtcag cccggaaccc tacttggcga tgatcaaatc    60

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
agcctactaa ttcgcgctga actaggtcag cccggaactc tacttggcga tgatcaaatc    60

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
agcctgctaa ttcgcgctga actaggtcag cccggaaccc tacttggcga tgatcaaatc    60

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
agcctactaa ttcgcgctga actaggtcag cccggaaccc tacttcccca tgatcaaatc    60

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
agcctactaa ttcgcgctga actaggtcag cccggaactt tacttggcga tgaccaaatc    60

<210> SEQ ID NO 12
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
ttgagcctac taattcgcgc tgaactaggt cagcccggaa ccctacttgg cgatgatcaa    60

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
ttgagcctac taattcgcgc tgaactaggt cagcccggaa ctctacttgg cgatgatcaa    60

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
ttgagcctgc taattcgcgc tgaactaggt cagcccggaa ccctacttgg cgatgatcaa    60

<210> SEQ ID NO 15
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
ttgagcctac taattcgcgc tgaactaggt cagcccggaa ccctacttcc ccatgatcaa    60

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
ttaagcctac taattcgcgc tgaactaggt cagcccggaa ctttacttgg cgatgaccaa    60

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
tgagcctact aattcgcgct gaactaggtc agcccggaac cctacttggc gatgatcaaa    60

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
tgagcctact aattcgcgct gaactaggtc agcccggaac tctacttggc gatgatcaaa    60

```
<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
tgagcctgct aattcgcgct gaactaggtc agcccggaac cctacttggc gatgatcaaa    60

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
tgagcctact aattcgcgct gaactaggtc agcccggaac cctacttccc catgatcaaa    60

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
taagcctact aattcgcgct gaactaggtc agcccggaac tttacttggc gatgaccaaa    60

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
gagcctacta attcgcgctg aactaggtca gcccggaacc ctacttggcg atgatcaaat    60

<210> SEQ ID NO 23
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
gagcctacta attcgcgctg aactaggtca gcccggaact ctacttggcg atgatcaaat    60

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
gagcctgcta attcgcgctg aactaggtca gcccggaacc ctacttggcg atgatcaaat    60

<210> SEQ ID NO 25
```

<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
gagcctacta attcgcgctg aactaggtca gcccggaacc ctacttcccc atgatcaaat    60

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
aagcctacta attcgcgctg aactaggtca gcccggaact ttacttggcg atgaccaaat    60

<210> SEQ ID NO 27
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
aagccggagc gggtactgga tgaactgtat acccaccttt agctggaaac ttagcccatg    60

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
aagccggggc gggtactgga tgaaccgtat acccaccttt agctggaaac ttagcccatg    60

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
aagccggggc gggtactgga tgaaccgtat acccaccttt agccggaaac ttagcccatg    60

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
aggccggagc gggtactgga tgaactgtat acccgccttt agctggaaac ttagcccacg    60

<210> SEQ ID NO 31
<211> LENGTH: 60

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
aggccggagc gggtactgga tgaactgtat acccacctt agctggaaac ttagcccacg    60

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
aagccggagc gggtactgga tgaaccgtat acccacctt agctggaaac ttagcccatg    60

<210> SEQ ID NO 33
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33 aagccgggc gggcactgga tgaaccgtat acccacctt agctggaaac ttagcccatg    60

<210> SEQ ID NO 34
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34 aagccgggc gggtaccgga tgaaccgtat acccacctt agctggaaac ttagcccatg    60

<210> SEQ ID NO 35
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35 aagccgggc gggtactgga tgagccgtat acccacctt agctggaaac ttagcccatg    60

<210> SEQ ID NO 36
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
aagccggagc gggtactgga tgaaccgtat acccacctt agctggaaac ttagcccatg    60

<210> SEQ ID NO 37
<211> LENGTH: 60
<212> TYPE: DNA

<213> ORGANISM: Artificial Sequence
<220> FEATURE:
<223> OTHER INFORMATION: Description of Artificial Sequence: Synthetic
      probe

<400> SEQUENCE: 37
aagccggggc gggtactgga tgaaccgtat acccaccttt agctggaaac ttagcccgtg    60

<210> SEQ ID NO 38
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
aagccggagc gggtactgga tgaactgtat atccaccttt agctggaaac ttggcccatg    60

<210> SEQ ID NO 39
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
aagccggggc gggtactgga tgaaccgaat acccaccctt agctggaaac ttagcccaag    60

<210> SEQ ID NO 40
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
aagccggggc gggtactgga tgaaccgtat acccaccttt agctggaaac ttaccccatg    60

<210> SEQ ID NO 41
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
ggcatcctca atagtagaag ccggagcggg tactggatga actgtatacc cacctttagc    60

<210> SEQ ID NO 42
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
ggcatcctca atagtagaag ccggggcggg tactggatga accgtatacc cacctttagc    60

<210> SEQ ID NO 43
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
ggcatcctca atagtagaag ccggggcggg cactggatga accgtatacc caccctttagc    60

<210> SEQ ID NO 44
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
ggcatcctca atagtagaag ccggggcggg tactggatga accgaatacc caccctttagc    60

<210> SEQ ID NO 45
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
ggcatcctca atagtaaaag ccggggcggg tactggatga accgtatacc caccctttagc    60

<210> SEQ ID NO 46
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
ggcatcctca atagtagaag ccggggcggg taccggatga accgtatacc caccctttagc    60

<210> SEQ ID NO 47
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
ggcatcctca atagtagaag ccggagcggg tactggatga accgtatacc caccctttagc    60

<210> SEQ ID NO 48
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
ggcatcctca atagtagaag ccggggcggg tactggatga gccgtatacc caccctttagc    60

<210> SEQ ID NO 49
<211> LENGTH: 60
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 49
ggcatcctca atagtagaag ccggagcggg tactggatga actgtatatc cacctttagc    60

<210> SEQ ID NO 50
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
ggcatcctca atagtagagg ccggagcggg tactggatga actgtatacc cgcctttagc    60

<210> SEQ ID NO 51
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
ggcatcctca atagtagagg ccggagcggg tactggatga actgtatacc cacctttagc    60

<210> SEQ ID NO 52
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
ggcgtcctca atagtagaag ccggagcggg tactggatga actgtatacc cacctttagc    60

<210> SEQ ID NO 53
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
caatagtaga agccggagcg ggtactggat gaactgtata cccacccttta gctggaaact    60 tagcccatgc                                                            70

<210> SEQ ID NO 54
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
caatagtaga agccggggcg ggtactggat gaaccgtata cccacccttta gctggaaact    60 tagcccatgc                                                            70

<210> SEQ ID NO 55
<211> LENGTH: 70

-continued

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
caatagtaga agccggagcg ggtactggat gaaccgtata cccacccttta gctggaaact    60 tagcccatgc                                                            70

<210> SEQ ID NO 56
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
caatagtaga ggccggagcg ggtactggat gaactgtata cccacccttta gctggaaact    60 tagcccacgc                                                            70

<210> SEQ ID NO 57
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
caatagtaga ggccggagcg ggtactggat gaactgtata cccgcccttta gctggaaact    60 tagcccacgc                                                            70

<210> SEQ ID NO 58
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
caatagtaga agccggggcg ggtactggat gagccgtata cccacccttta gctggaaact    60 tagcccatgc                                                            70

<210> SEQ ID NO 59
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
caatagtaga agccggggcg ggcactggat gaaccgtata cccacccttta gctggaaact    60 tagcccatgc                                                            70

<210> SEQ ID NO 60
<211> LENGTH: 70
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 60
caatagtaga agccggggcg ggtactggat gaaccgtata cccacctttta gctggaaact    60 tacccccatgc    70

<210> SEQ ID NO 61
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 61
caatagtaga agccggggcg ggtactggat gaaccgaata cccacccttta gctggaaact    60 tagcccaagc    70

<210> SEQ ID NO 62
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 62
caatagtaga agccggggcg ggtactggat gaaccgtata cccacctttta gctggaaact    60 tagcccgtgc    70

<210> SEQ ID NO 63
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 63
caatagtaga agccggggcg ggtactggat gaaccgtata cccacctttta gccggaaact    60 tagcccatgc    70

<210> SEQ ID NO 64
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 64
caatagtaga agccggggcg ggtaccggat gaaccgtata cccacctttta gctggaaact    60 tagcccatgc    70

<210> SEQ ID NO 65
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
caatagtaaa agccggggcg ggtactggat gaaccgtata cccaccttta gctggaaact    60
tagcccatgc                                                          70

<210> SEQ ID NO 66
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
caatagtaga agccggagcg ggtactggat gaactgtata tccaccttta gctggaaact    60
tggcccatgc                                                          70

<210> SEQ ID NO 67
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 67
atagtagaag ccggagcggg tactggatga actgtatacc caccttagc tggaaactta    60 gcccatgcag                                                          70

<210> SEQ ID NO 68
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
atagtagaag ccggggcggg tactggatga accgtatacc caccttagc tggaaactta    60 gcccatgcag                                                          70

<210> SEQ ID NO 69
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 69
atagtagagg ccggagcggg tactggatga actgtatacc cacctttagc tggaaactta    60
gcccacgcag                                                          70

<210> SEQ ID NO 70
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 70
atagtagagg ccggagcggg tactggatga actgtatacc cgcctttagc tggaaactta    60
gcccacgcag                                                          70

<210> SEQ ID NO 71
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
atagtagaag ccggggcggg tactggatga gccgtatacc cacctttagc tggaaactta    60
gcccatgcag                                                            70

<210> SEQ ID NO 72
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 72
atagtagaag ccggggcggg cactggatga accgtatacc cacctttagc tggaaactta    60
gcccatgcag                                                            70

<210> SEQ ID NO 73
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
atagtagaag ccggggcggg tactggatga accgtatacc cacctttagc tggaaactta    60
ccccatgcag                                                            70

<210> SEQ ID NO 74
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
atagtagaag ccggggcggg tactggatga accgaatacc cacccttagc tggaaactta    60
gcccaagcag                                                            70

<210> SEQ ID NO 75
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75
atagtagaag ccggggcggg tactggatga accgtatacc cacctttagc tggaaactta    60
gcccgtgcag                                                            70

<210> SEQ ID NO 76
<211> LENGTH: 70
<212> TYPE: DNA

<213> ORGANISM: Artificial Sequence
<220> FEATURE:
<223> OTHER INFORMATION: Description of Artificial Sequence: Synthetic probe

<400> SEQUENCE: 76 atagtagaaag ccggggcggg tactggatga accgtatacc cacctttagc cggaaactta     60
gcccatgcag                                                             70

<210> SEQ ID NO 77
<211> LENGTH: 70
<212> TYPE: DNA
<213> ORGANISM: Artificial Sequence
<220> FEATURE:
<223> OTHER INFORMATION: Description of Artificial Sequence: Synthetic probe

<400> SEQUENCE: 77 atagtagaaag ccggggcggg taccggatga accgtatacc cacctttagc tggaaactta     60
gcccatgcag                                                             70

<210> SEQ ID NO 78
<211> LENGTH: 70
<212> TYPE: DNA
<213> ORGANISM: Artificial Sequence
<220> FEATURE:
<223> OTHER INFORMATION: Description of Artificial Sequence: Synthetic probe

<400> SEQUENCE: 78 atagtaaaaag ccggggcggg tactggatga accgtatacc cacctttagc tggaaactta     60
gcccatgcag                                                             70

<210> SEQ ID NO 79
<211> LENGTH: 70
<212> TYPE: DNA
<213> ORGANISM: Artificial Sequence
<220> FEATURE:
<223> OTHER INFORMATION: Description of Artificial Sequence: Synthetic probe

<400> SEQUENCE: 79 atagtagaaag ccggagcggg tactggatga actgtatatc cacctttagc tggaaacttg     60
gcccatgcag                                                             70

<210> SEQ ID NO 80
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 80
gcccatgcag gagcctcagt agatctaact attttctccc tacatctggc aggtgtctct     60

<210> SEQ ID NO 81
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 81
gcccatgcag gagcctcagt agacctaact attttctccc tacacctggc aggtgtctct    60

<210> SEQ ID NO 82
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82
gcccatgcag gagcctcagt agatctaatt attttctccc tacacctggc aggtgtctct    60

<210> SEQ ID NO 83
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
gcccatgcag gagcctcagt agatctaact attttctccc tacacctggc aggtgtctct    60

<210> SEQ ID NO 84
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
agcccatgca ggagcctcag tagatctaac tattttctcc ctacatctgg caggtgtctc    60

<210> SEQ ID NO 85
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
agcccatgca ggagcctcag tagacctaac tattttctcc ctacacctgg caggtgtctc    60

<210> SEQ ID NO 86
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 86
agcccatgca ggagcctcag tagatctaat tattttctcc ctacacctgg caggtgtctc    60

<210> SEQ ID NO 87
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
agcccatgca ggagcctcag tagatctaac tattttctcc ctacacctgg caggtgtctc       60

<210> SEQ ID NO 88
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 88
ctagcccatg caggagcctc agtagatcta actattttct ccctacatct ggcaggtgtc       60

<210> SEQ ID NO 89
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89
ctagcccatg caggagcctc agtagaccta actattttct ccctacacct ggcaggtgtc       60

<210> SEQ ID NO 90
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
ctagcccatg caggagcctc agtagatcta attattttct ccctacacct ggcaggtgtc       60

<210> SEQ ID NO 91
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 91
ctagcccatg caggagcctc agtagatcta actattttct ccctacacct ggcaggtgtc       60

<210> SEQ ID NO 92
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 92
cctagcccat gcaggagcct cagtagatct aactattttc tccctacatc tggcaggtgt       60

<210> SEQ ID NO 93
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 93
cctagcccat gcaggagcct cagtagacct aactattttc tccctacacc tggcaggtgt       60

<210> SEQ ID NO 94
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 94
cctagcccat gcaggagcct cagtagatct aattattttc tccctacacc tggcaggtgt    60

<210> SEQ ID NO 95
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
cctagcccat gcaggagcct cagtagatct aactattttc tccctacacc tggcaggtgt    60

<210> SEQ ID NO 96
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 96
gcaacctagc ccatgcagga gcctcagtag atctaactat tttctcccta catctggcag    60
gtgtctcttc                                                          70

<210> SEQ ID NO 97
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97
gcaacctagc ccatgcagga gcctcagtag atctaactat tttctcccta cacctggcag    60
gtgtctcttc                                                          70

<210> SEQ ID NO 98
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98
gcaacctagc ccatgcagga gcctcagtag atctaattat tttctcccta cacctggcag    60
gtgtctcttc                                                          70

<210> SEQ ID NO 99
<211> LENGTH: 70
<212> TYPE: DNA
<213> ORGANISM: Artificial Sequence
<220> FEATURE:
<223> OTHER INFORMATION: Description of Artificial Sequence: Synthetic probe

<400> SEQUENCE: 99
gcaacctagc ccatgcagga gcctcagtag acctaactat tttctcccta cacctggcag    60
gtgtctcttc    70

<210> SEQ ID NO 100
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100
ggcaacctag cccatgcagg agcctcagta gatctaacta ttttctccct acatctggca    60
ggtgtctctt    70

<210> SEQ ID NO 101
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
ggcaacctag cccatgcagg agcctcagta gatctaacta ttttctccct acacctggca    60
ggtgtctctt    70

<210> SEQ ID NO 102
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
ggcaacctag cccatgcagg agcctcagta gatctaatta ttttctccct acacctggca    60
ggtgtctctt    70

<210> SEQ ID NO 103
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 103
ggcaacctag cccatgcagg agcctcagta gacctaacta ttttctccct acacctggca    60
ggtgtctctt    70

<210> SEQ ID NO 104
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104
tgaaccgtat atcctcctct agctggaaat ctggcgcatg caggagcctc tgttgactta    60

<210> SEQ ID NO 105
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
gaaccgtata tcctcctcta gctggaaatc tggcgcatgc aggagcctct gttgacttaa    60

<210> SEQ ID NO 106
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 106
ctgaaccgta tatcctcctc tagctggaaa tctggcgcat gcaggagcct ctgttgactt    60

<210> SEQ ID NO 107
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107
aaccgtatat cctcctctag ctggaaatct ggcgcatgca ggagcctctg ttgacttaac    60

<210> SEQ ID NO 108
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
cctctagctg gaaatctggc gcatgcagga gcctctgttg acttaaccat tttctctctc    60

<210> SEQ ID NO 109
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
ctctagctgg aaatctggcg catgcaggag cctctgttga cttaaccatt ttctctctcc    60

<210> SEQ ID NO 110
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 110
ctagctggaa atctggcgca tgcaggagcc tctgttgact taaccatttt ctctctccac    60

<210> SEQ ID NO 111
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111
gctggaaatc tggcgcatgc aggagcctct gttgacttaa ccatttctc tctccaccta       60

<210> SEQ ID NO 112
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 112
gctggaaatc tggcgcatgc aggagcctct gttgacttaa ccatttctc tctccacctg       60

<210> SEQ ID NO 113
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 113
ctggaaatct ggcgcatgca ggagcctctg ttgacttaac catttctct ctccacctag       60

<210> SEQ ID NO 114
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 114
ctggaaatct ggcgcatgca ggagcctctg ttgacttaac catttctct ctccacctgg       60

<210> SEQ ID NO 115
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 115
tggaaatctg gcgcatgcag gagcctctgt tgacttaacc attttctctc tccacctagc     60

<210> SEQ ID NO 116
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 116
tggaaatctg gcgcatgcag gagcctctgt tgacttaacc attttctctc tccacctggc     60

<210> SEQ ID NO 117
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 117
ggaaatctgg cgcatgcagg agcctctgtt gacttaacca ttttctctct ccacctagct    60

<210> SEQ ID NO 118
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 118
ggaaatctgg cgcatgcagg agcctctgtt gacttaacca ttttctctct ccacctggct    60

<210> SEQ ID NO 119
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 119
gaaatctggc gcatgcagga gcctctgttg acttaaccat tttctctctc cacctagctg    60

<210> SEQ ID NO 120
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 120
gaaatctggc gcatgcagga gcctctgttg acttaaccat tttctctctc cacctggctg    60

<210> SEQ ID NO 121
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 121
tcctcctcta gctggaaatc tggcgcatgc aggagcctct gttgacttaa ccattttctc    60

<210> SEQ ID NO 122
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 122
cctcctctag ctggaaatct ggcgcatgca ggagcctctg ttgacttaac cattttctct    60

<210> SEQ ID NO 123
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 123
ctcctctagc tggaaatctg gcgcatgcag gagcctctgt tgacttaacc attttctctc    60

<210> SEQ ID NO 124
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 124
cgtatatcct cctctagctg gaaatctggc gcatgcagga gcctctgttg acttaaccat    60

<210> SEQ ID NO 125
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 125
accgtatatc ctcctctagc tggaaatctg gcgcatgcag gagcctctgt tgacttaacc    60

<210> SEQ ID NO 126
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 126
ccgtatatcc tcctctagct ggaaatctgg cgcatgcagg agcctctgtt gacttaacca    60

<210> SEQ ID NO 127
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 127
tatcctcctc tagctggaaa tctggcgcat gcaggagcct ctgttgactt aaccattttc    60
tctctccacc                                                           70

<210> SEQ ID NO 128
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 128
atcctcctct agctggaaat ctggcgcatg caggagcctc tgttgactta accattttct    60
ctctccacct 70

<210> SEQ ID NO 129
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 129
ggctgaaccg tatatcctcc tctagctgga aatctggcgc atgcaggagc ctctgttgac    60
ttaaccattt    70

<210> SEQ ID NO 130
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 130
aggctgaacc gtatatcctc ctctagctgg aaatctggcg catgcaggag cctctgttga    60
cttaaccatt    70

<210> SEQ ID NO 131
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 131
cctctagctg gaaatctggc gcatgcagga gcctctgttg acttaaccat tttctctctc    60
cacctagctg    70

<210> SEQ ID NO 132
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 132
cctctagctg gaaatctggc gcatgcagga gcctctgttg acttaaccat tttctctctc    60
cacctggctg    70

<210> SEQ ID NO 133
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 133
tcctcctcta gctggaaatc tggcgcatgc aggagcctct gttgacttaa ccattttctc    60
tctccaccta    70

<210> SEQ ID NO 134

```
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 134
tcctcctcta gctggaaatc tggcgcatgc aggagcctct gttgacttaa ccatttctc    60 tctccacctg                                                          70

<210> SEQ ID NO 135
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 135
tcctctagct ggaaatctgg cgcatgcagg agcctctgtt gacttaacca ttttctctct    60
ccacctagct                                                          70

<210> SEQ ID NO 136
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 136
tcctctagct ggaaatctgg cgcatgcagg agcctctgtt gacttaacca ttttctctct    60
ccacctggct                                                          70

<210> SEQ ID NO 137
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 137
cctcctctag ctggaaatct ggcgcatgca ggagcctctg ttgacttaac cattttctct    60
ctccacctag                                                          70

<210> SEQ ID NO 138
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 138
cctcctctag ctggaaatct ggcgcatgca ggagcctctg ttgacttaac cattttctct    60
ctccacctgg                                                          70

<210> SEQ ID NO 139
<211> LENGTH: 70
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 139
ctcctctagc tggaaatctg gcgcatgcag gagcctctgt tgacttaacc attttctctc    60
tccacctagc                                                           70

<210> SEQ ID NO 140
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 140
ctcctctagc tggaaatctg gcgcatgcag gagcctctgt tgacttaacc attttctctc    60
tccacctggc                                                           70

<210> SEQ ID NO 141
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 141
cctcctcatc cgagccgaac taggtcagcc cggtacttta ctaggtgacg atcaaattta    60

<210> SEQ ID NO 142
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 142
cctcctcatc cgagccgaac taggtcagcc cggtacttta ctaggtgatg atcaaattta    60

<210> SEQ ID NO 143
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 143
cctcctcatc cgagccgaac taggtcagcc cggtacttta ctaggcgacg atcaaattta    60

<210> SEQ ID NO 144
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 144
cctcctcatc cgggccgaac taggtcagcc cggtacttta ctaggtgacg atcaaattta    60

<210> SEQ ID NO 145
<211> LENGTH: 60
```

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 145
cctcctcatc cgagccgaac taggtcagcc cggtacttta ctaggagacg atcagattta      60

<210> SEQ ID NO 146
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 146
agcctcctca tccgagccga actaggtcag cccggtactt tactaggtga cgatcaaatt      60

<210> SEQ ID NO 147
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 147
agcctcctca tccgagccga actaggtcag cccggtactt tactaggtga tgatcaaatt      60

<210> SEQ ID NO 148
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 148
agcctcctca tccgagccga actaggtcag cccggtactt tactaggcga cgatcaaatt      60

<210> SEQ ID NO 149
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 149
agcctcctca tccgggccga actaggtcag cccggtactt tactaggtga cgatcaaatt      60

<210> SEQ ID NO 150
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 150
agcctcctca tccgagccga actaggtcag cccggtactt tactaggaga cgatcagatt      60

<210> SEQ ID NO 151
<211> LENGTH: 60
<212> TYPE: DNA

<213> ORGANISM: Artificial Sequence
<220> FEATURE:
<223> OTHER INFORMATION: Description of Artificial Sequence: Synthetic
      probe

<400> SEQUENCE: 151
gcctcctcat ccgagccgaa ctaggtcagc ccggtacttt actaggtgac gatcaaattt    60

<210> SEQ ID NO 152
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 152
gcctcctcat ccgagccgaa ctaggtcagc ccggtacttt actaggtgat gatcaaattt    60

<210> SEQ ID NO 153
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 153
gcctcctcat ccgagccgaa ctaggtcagc ccggtacttt actaggcgac gatcaaattt    60

<210> SEQ ID NO 154
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 154
gcctcctcat ccgggccgaa ctaggtcagc ccggtacttt actaggtgac gatcaaattt    60

<210> SEQ ID NO 155
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 155
cactgctttg agcctcctca tccgagccga actaggtcag cccggtactt tactaggtga    60
cgatcaaatt                                                            70

<210> SEQ ID NO 156
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 156
cactgccttg agcctcctca tccgagccga actaggtcag cccggtactt tactaggtga    60
cgatcaaatt                                                            70

```
<210> SEQ ID NO 157
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 157
cactgccttg agcctcctca tccgagccga actaggtcag cccggtactt tactaggtga     60
tgatcaaatt                                                             70

<210> SEQ ID NO 158
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 158
cactgccttg agcctcctca tccgagccga actaggtcag cccggtactt tactaggcga     60
cgatcaaatt                                                             70

<210> SEQ ID NO 159
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 159
cactgccttg agcctcctca tccgagccga gctaggtcag cccggtactt tactaggcga     60
cgaccaaatt                                                             70

<210> SEQ ID NO 160
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 160
ctgctttgag cctcctcatc cgagccgaac taggtcagcc cggtacttta ctaggtgacg     60
atcaaattta                                                             70

<210> SEQ ID NO 161
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 161
ctgccttgag cctcctcatc cgagccgaac taggtcagcc cggtacttta ctaggtgacg     60
atcaaattta                                                             70

<210> SEQ ID NO 162
<211> LENGTH: 70
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 162
ctgccttgag cctcctcatc cgagccgaac taggtcagcc cggtacttta ctaggtgatg    60
atcaaattta                                                           70

<210> SEQ ID NO 163
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 163
ctgccttgag cctcctcatc cgagccgaac taggtcagcc cggtacttta ctaggcgacg    60
atcaaattta                                                           70

<210> SEQ ID NO 164
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 164
ctgccttgag cctcctcatc cgagccgagc taggtcagcc cggtacttta ctaggcgacg    60
accaaattta                                                           70

<210> SEQ ID NO 165
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 165
actgctttga gcctcctcat ccgagccgaa ctaggtcagc ccggtacttt actaggtgac    60
gatcaaattt                                                           70

<210> SEQ ID NO 166
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 166
actgccttga gcctcctcat ccgagccgaa ctaggtcagc ccggtacttt actaggtgac    60
gatcaaattt                                                           70

<210> SEQ ID NO 167
<211> LENGTH: 70
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 167
actgccttga gcctcctcat ccgagccgaa ctaggtcagc ccggtacttt actaggtgat    60
gatcaaattt                                                            70

<210> SEQ ID NO 168
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 168
actgccttga gcctcctcat ccgagccgaa ctaggtcagc ccggtacttt actaggcgac    60
gatcaaattt                                                            70

<210> SEQ ID NO 169
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 169
actgccttga gcctcctcat ccgagccgag ctaggtcagc ccggtacttt actaggcgac    60
gaccaaattt                                                            70

<210> SEQ ID NO 170
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 170
caatagtaga agcaggagca ggaacaggat gaacagtcta cccacctcta gccggaaatc    60

<210> SEQ ID NO 171
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 171
tagtagaagc aggagcagga acaggatgaa cagtctaccc acctctagcc ggaaatctag    60

<210> SEQ ID NO 172
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 172
tagtagaagc aggagcagga acaggatgaa cagtctaccc acctctagcc ggaaatccag    60

<210> SEQ ID NO 173
<211> LENGTH: 60
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 173
agtagaagca ggagcaggaa caggatgaac agtctaccca cctctagccg gaaatctagc    60

<210> SEQ ID NO 174
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 174
agtagaagca ggagcaggaa caggatgaac agtctaccca cctctagccg gaaatccagt    60

<210> SEQ ID NO 175
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 175
gtctacccac ctctagccgg aaatctagcc catgcaggag catcagtaga cctaacaatt    60

<210> SEQ ID NO 176
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 176
gtctacccac ctctagccgg aaatccagtc catgcaggag catcagtaga cctaacaatt    60

<210> SEQ ID NO 177
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 177
gtctacccac ctctagccgg aaatctagcc catgcaggag catcagtaga tctaacaatt    60

<210> SEQ ID NO 178
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 178
cccacctcta gccggaaatc tagcccatgc aggagcatca gtagacctaa caattttctc    60

<210> SEQ ID NO 179
<211> LENGTH: 60
<212> TYPE: DNA
<213> ORGANISM: Artificial Sequence
```

-continued

<220> FEATURE:
<223> OTHER INFORMATION: Description of Artificial Sequence: Synthetic
      probe

<400> SEQUENCE: 179
cccacctcta gccggaaatc cagtccatgc aggagcatca gtagacctaa caattttctc    60

<210> SEQ ID NO 180
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 180
cccacctcta gccggaaatc tagcccatgc aggagcatca gtagatctaa caattttctc    60

<210> SEQ ID NO 181
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 181
ccacctctag ccggaaatct agcccatgca ggagcatcag tagacctaac aattttctcc    60

<210> SEQ ID NO 182
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 182
ccacctctag ccggaaatcc agtccatgca ggagcatcag tagacctaac aattttctcc    60

<210> SEQ ID NO 183
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 183
ccacctctag ccggaaatct agcccatgca ggagcatcag tagatctaac aattttctcc    60

<210> SEQ ID NO 184
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 184
aggatgaaca gtctacccac ctctagccgg aaatctagcc catgcaggag catcagtaga    60

<210> SEQ ID NO 185
<211> LENGTH: 60
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 185
aggatgaaca gtctacccac ctctagccgg aaatccagtc catgcaggag catcagtaga      60

<210> SEQ ID NO 186
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 186
aggatgaacc gtatatccac ctttagccgg aaatttagcc cacgccggag catcagtgga      60

<210> SEQ ID NO 187
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 187
agtctaccca cctctagccg gaaatctagc ccatgcagga gcatcagtag acctaacaat      60

<210> SEQ ID NO 188
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 188
agtctaccca cctctagccg gaaatccagt ccatgcagga gcatcagtag acctaacaat      60

<210> SEQ ID NO 189
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 189
agtctaccca cctctagccg gaaatctagc ccatgcagga gcatcagtag atctaacaat      60

<210> SEQ ID NO 190
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 190
atgaacagtc tacccacctc tagccggaaa tctagcccat gcaggagcat cagtagacct      60

<210> SEQ ID NO 191
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 191
atgaacagtc tacccacctc tagccggaaa tccagtccat gcaggagcat cagtagacct    60

<210> SEQ ID NO 192
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 192
atgaacagtc tacccacctc tagccggaaa tctagcccat gcaggagcat cagtagatct    60

<210> SEQ ID NO 193
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 193
tgaacagtct acccacctct agccggaaat ctagcccatg caggagcatc agtagaccta    60

<210> SEQ ID NO 194
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 194
tgaacagtct acccacctct agccggaaat ccagtccatg caggagcatc agtagaccta    60

<210> SEQ ID NO 195
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 195
tgaacagtct acccacctct agccggaaat ctagcccatg caggagcatc agtagatcta    60

<210> SEQ ID NO 196
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 196
gaacagtcta cccacctcta gccggaaatc tagcccatgc aggagcatca gtagacctaa    60

<210> SEQ ID NO 197
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 197
gaacagtcta cccacctcta gccggaaatc cagtccatgc aggagcatca gtagacctaa        60

<210> SEQ ID NO 198
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 198
gaacagtcta cccacctcta gccggaaatc tagcccatgc aggagcatca gtagatctaa        60

<210> SEQ ID NO 199
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 199
aacagtctac ccacctctag ccggaaatct agcccatgca ggagcatcag tagacctaac        60

<210> SEQ ID NO 200
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 200
aacagtctac ccacctctag ccggaaatcc agtccatgca ggagcatcag tagacctaac        60

<210> SEQ ID NO 201
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 201
aacagtctac ccacctctag ccggaaatct agcccatgca ggagcatcag tagatctaac        60

<210> SEQ ID NO 202
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 202
acagtctacc cacctctagc cggaaatcta gcccatgcag gagcatcagt agacctaaca        60

<210> SEQ ID NO 203
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 203
acagtctacc cacctctagc cggaaatcca gtccatgcag gagcatcagt agacctaaca    60

<210> SEQ ID NO 204
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 204
acagtctacc cacctctagc cggaaatcta gcccatgcag gagcatcagt agatctaaca    60

<210> SEQ ID NO 205
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 205
cagtctaccc acctctagcc ggaaatctag cccatgcagg agcatcagta gacctaacaa    60

<210> SEQ ID NO 206
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 206
cagtctaccc acctctagcc ggaaatccag tccatgcagg agcatcagta gacctaacaa    60

<210> SEQ ID NO 207
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 207
cagtctaccc acctctagcc ggaaatctag cccatgcagg agcatcagta gatctaacaa    60

<210> SEQ ID NO 208
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 208
tcaatagtag aagcaggagc aggaacagga tgaacagtct acccacctct agccggaaat    60
ctagcccatg                                                          70

<210> SEQ ID NO 209
<211> LENGTH: 70
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 209
tcaatagtag aagcaggagc aggaacagga tgaacagtct acccacctct agccggaaat    60
ccagtccatg                                                          70

<210> SEQ ID NO 210
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 210
caatagtaga agcaggagca ggaacaggat gaacagtcta cccacctcta gccggaaatc    60
tagcccatgc                                                          70

<210> SEQ ID NO 211
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 211
caatagtaga agcaggagca ggaacaggat gaacagtcta cccacctcta gccggaaatc    60
cagtccatgc                                                          70

<210> SEQ ID NO 212
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 212
gtctacccac ctctagccgg aaatctagcc catgcaggag catcagtaga cctaacaatt    60
ttctcccttc                                                          70

<210> SEQ ID NO 213
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 213
gtctacccac ctctagccgg aaatctagcc catgcaggag catcagtaga cctaacaatt    60
ttctccctcc                                                          70

<210> SEQ ID NO 214
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 214
gtctacccac ctctagccgg aaatctagcc catgcaggag catcagtaga tctaacaatt    60
```
ttctcccttc                                                            70

<210> SEQ ID NO 215
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 215
gtctacccac ctctagccgg aaatccagtc catgcaggag catcagtaga cctaacaatt     60
ttctcccttc                                                            70

<210> SEQ ID NO 216
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 216
caggatgaac agtctaccca cctctagccg gaaatctagc ccatgcagga gcatcagtag     60
acctaacaat                                                            70

<210> SEQ ID NO 217
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 217
caggatgaac agtctaccca cctctagccg gaaatctagc ccatgcagga gcatcagtag     60
atctaacaat                                                            70

<210> SEQ ID NO 218
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 218
caggatgaac agtctaccca cctctagccg gaaatccagt ccatgcagga gcatcagtag     60
acctaacaat                                                            70

<210> SEQ ID NO 219
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 219
gagcttctga ctcctccctc catcctttct actcttactc gcctcatcta tggtagaagc     60

<210> SEQ ID NO 220
<211> LENGTH: 60

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 220
gagcttctga ctcctccccc catcctttct actcttactc gcctcatcta tggtagaagc     60

<210> SEQ ID NO 221
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 221
gagcttctga ctcctccctc catcctttct actcctactc gcctcatcta tggtagaagc     60

<210> SEQ ID NO 222
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 222
ctccctccat cctttctact cttactcgcc tcatctatgg tagaagccgg agcaggaact     60

<210> SEQ ID NO 223
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 223
ctccccccat cctttctact cttactcgcc tcatctatgg tagaagccgg agcaggaact     60

<210> SEQ ID NO 224
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 224
ctccctccat cctttctact cctactcgcc tcatctatgg tagaagccgg agcaggaact     60

<210> SEQ ID NO 225
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 225
tcctccctcc atcctttcta ctcttactcg cctcatctat ggtagaagcc ggagcaggaa     60

<210> SEQ ID NO 226
<211> LENGTH: 60
<212> TYPE: DNA
```

<213> ORGANISM: Artificial Sequence
<220> FEATURE:
<223> OTHER INFORMATION: Description of Artificial Sequence: Synthetic probe

<400> SEQUENCE: 226
tcctcccccc atcctttcta ctcttactcg cctcatctat ggtagaagcc ggagcaggaa    60

<210> SEQ ID NO 227
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 227
tcctccctcc atcctttcta ctcctactcg cctcatctat ggtagaagcc ggagcaggaa    60

<210> SEQ ID NO 228
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 228
tgactcctcc ctccatcctt tctactctta ctcgcctcat ctatggtaga agccggagca    60

<210> SEQ ID NO 229
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 229
tgactcctcc cccatcctt tctactctta ctcgcctcat ctatggtaga agccggagca    60

<210> SEQ ID NO 230
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 230
tgactcctcc ctccatcctt tctactccta ctcgcctcat ctatggtaga agccggagca    60

<210> SEQ ID NO 231
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 231
gctcctgaca tagcatttcc ccgaataaac aacatgagct tctgactcct ccctccatcc    60

<210> SEQ ID NO 232
<211> LENGTH: 60
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 232
gctcctgaca tagcatttcc ccgaataaac aacatgagct tctgactcct cccccatcc      60

<210> SEQ ID NO 233
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 233
atgagcttct gactcctccc tccatccttt ctactcttac tcgcctcatc tatggtagaa      60
gccggagcag                                                            70

<210> SEQ ID NO 234
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 234
atgagcttct gactccccccc cccatccttt ctactcttac tcgcctcatc tatggtagaa     60
gccggagcag                                                            70

<210> SEQ ID NO 235
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 235
atgagcttct gactcctccc tccatccttt ctactcctac tcgcctcatc tatggtagaa      60
gccggagcag                                                            70

<210> SEQ ID NO 236
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 236
agcttctgac tcctccctcc atcctttcta ctcttactcg cctcatctat ggtagaagcc      60
ggagcaggaa                                                            70

<210> SEQ ID NO 237
<211> LENGTH: 70
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 237
agcttctgac tccccccccc atcctttcta ctcttactcg cctcatctat ggtagaagcc    60
ggagcaggaa                                                          70

<210> SEQ ID NO 238
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 238
agcttctgac tcctccctcc atcctttcta ctcctactcg cctcatctat ggtagaagcc    60
ggagcaggaa                                                          70

<210> SEQ ID NO 239
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 239
cttctgactc ctccctccat cctttctact cttactcgcc tcatctatgg tagaagccgg    60
agcaggaact                                                          70

<210> SEQ ID NO 240
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 240
cttctgactc ccccccccat cctttctact cttactcgcc tcatctatgg tagaagccgg    60
agcaggaact                                                          70

<210> SEQ ID NO 241
<211> LENGTH: 70
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 241
cttctgactc ctccctccat cctttctact cctactcgcc tcatctatgg tagaagccgg    60
agcaggaact                                                          70